US011103664B2

(12) United States Patent
Lucey et al.

(10) Patent No.: US 11,103,664 B2
(45) Date of Patent: Aug. 31, 2021

(54) METHODS AND SYSTEMS FOR PROVIDING INTERFACE COMPONENTS FOR RESPIRATORY THERAPY

(71) Applicant: ResMed Pty Ltd, Bella Vista (AU)

(72) Inventors: Simon Michael Lucey, Pittsburgh, PA (US); Benjamin Peter Johnston, Sydney (AU); Priyanshu Gupta, Sydney (AU); Tzu-Chin Yu, Sydney (AU)

(73) Assignee: ResMed Pty Ltd

( * ) Notice: Subject to any disclaimer, the term of this patent is extended or adjusted under 35 U.S.C. 154(b) by 0 days.

(21) Appl. No.: 16/150,386

(22) Filed: Oct. 3, 2018

(65) Prior Publication Data

US 2019/0167934 A1    Jun. 6, 2019

Related U.S. Application Data

(63) Continuation of application No. 15/344,761, filed on Nov. 7, 2016, now Pat. No. 10,220,172.
(Continued)

(51) Int. Cl.
*A61M 16/06* (2006.01)
*G06N 20/00* (2019.01)
(Continued)

(52) U.S. Cl.
CPC ....... *A61M 16/0605* (2014.02); *A61B 5/0064* (2013.01); *A61B 5/1072* (2013.01);
(Continued)

(58) Field of Classification Search
None
See application file for complete search history.

(56) References Cited

U.S. PATENT DOCUMENTS 5,852,672 A * 12/1998 Lu .................. G01B 11/2441
                                              382/154
6,012,034 A    1/2000 Hamparian et al.
(Continued)

FOREIGN PATENT DOCUMENTS

CN    102609942 A    7/2012
CN    102802520 A    11/2012
(Continued)

OTHER PUBLICATIONS

EP Search Report for Application No. 16200746.2 dated May 24, 2017.
(Continued)

*Primary Examiner* — Jason A Pringle-Parker
(74) *Attorney, Agent, or Firm* — Botos Churchill IP Law LLP

(57) ABSTRACT

Systems and methods permit generation of a digital scan of a user's face such as for obtaining of a patient respiratory mask, or component(s) thereof, based on the digital scan. The method may include: receiving video data comprising a plurality of video frames of the user's face taken from a plurality of angles relative to the user's face, generating a three-dimensional representation of a surface of the user's face based on the plurality of video frames, receiving scale estimation data associated with the received video data, the scale estimation data indicative of a relative size of the user's face, and scaling the digital three-dimensional representation of the user's face based on the scale estimation data. In some aspects, the scale estimation data may be derived from motion information collected by the same device that collects the scan of the user's face.

32 Claims, 20 Drawing Sheets

Related U.S. Application Data

(60) Provisional application No. 62/259,743, filed on Nov. 25, 2015.

(51) Int. Cl.

| | | |
|---|---|---|
| *A61M 16/08* | (2006.01) | |
| *G06K 9/00* | (2006.01) | |
| *G06K 9/42* | (2006.01) | |
| *A61B 5/00* | (2006.01) | |
| *A61B 5/107* | (2006.01) | |
| *A61M 16/00* | (2006.01) | |
| *G16H 50/50* | (2018.01) | |
| *G16H 30/40* | (2018.01) | |
| *G16H 20/40* | (2018.01) | |
| *G06N 20/10* | (2019.01) | |
| *G06T 15/20* | (2011.01) | |
| *A61B 5/08* | (2006.01) | |
| *G06N 3/00* | (2006.01) | |
| *G16H 10/60* | (2018.01) | |

(52) U.S. Cl.
CPC ......... *A61B 5/1079* (2013.01); *A61M 16/021* (2017.08); *A61M 16/06* (2013.01); *A61M 16/0633* (2014.02); *A61M 16/0683* (2013.01); *A61M 16/0816* (2013.01); *G06K 9/00248* (2013.01); *G06K 9/00255* (2013.01); *G06K 9/00275* (2013.01); *G06K 9/00281* (2013.01); *G06K 9/42* (2013.01); *G06N 20/00* (2019.01); *G06N 20/10* (2019.01); *G06T 15/205* (2013.01); *G16H 20/40* (2018.01); *G16H 30/40* (2018.01); *G16H 50/50* (2018.01); *A61B 5/08* (2013.01); *A61M 2016/0661* (2013.01); *A61M 2205/3561* (2013.01); *A61M 2205/3592* (2013.01); *A61M 2205/505* (2013.01); *A61M 2207/00* (2013.01); *G06K 9/00201* (2013.01); *G06N 3/00* (2013.01); *G06T 2210/41* (2013.01); *G06T 2215/16* (2013.01); *G16H 10/60* (2018.01)

(56) References Cited

U.S. PATENT DOCUMENTS

| | | |
|---|---|---|
| 6,397,847 B1 | 6/2002 | Scarberry et al. |
| 6,569,097 B1 | 5/2003 | McMorrow et al. |
| 6,611,846 B1 | 8/2003 | Stoodley |
| 7,189,205 B2 | 3/2007 | McMorrow et al. |
| 7,583,275 B2 | 9/2009 | Neumann et al. |
| 7,672,973 B2 | 3/2010 | Lordo |
| 7,697,748 B2 | 4/2010 | Dimsdale et al. |
| 7,827,038 B2 | 11/2010 | Richard et al. |
| 7,848,698 B2 | 12/2010 | Batcheller et al. |
| 7,944,547 B2 | 5/2011 | Wang |
| 7,991,222 B2 | 8/2011 | Dimsdale et al. |
| 8,081,921 B2 | 12/2011 | Batcheller et al. |
| 8,165,844 B2 | 4/2012 | Luinge et al. |
| 8,204,299 B2 | 6/2012 | Arcas et al. |
| 8,207,964 B1 | 6/2012 | Meadow et al. |
| 8,265,542 B2 | 9/2012 | Batcheller et al. |
| 8,526,677 B1 | 9/2013 | Crichton et al. |
| 8,570,320 B2 | 10/2013 | Izadi et al. |
| 8,711,206 B2 | 4/2014 | Newcombe et al. |
| 8,810,632 B2 | 8/2014 | Hwang et al. |
| 8,838,381 B1 | 9/2014 | Daily et al. |
| 8,875,655 B2 | 11/2014 | Pettersson et al. |
| 8,878,905 B2 | 11/2014 | Fisker et al. |
| 8,909,325 B2 | 12/2014 | Kimchy et al. |
| 8,958,980 B2 | 2/2015 | Miksa et al. |
| 8,988,426 B2 | 3/2015 | Chen et al. |
| 9,041,915 B2 | 5/2015 | Earhart et al. |
| 9,107,613 B2 | 8/2015 | Firth et al. |
| 9,586,017 B2 | 3/2017 | Znamenskiy et al. |
| 9,697,599 B2 | 7/2017 | Prasad et al. |
| 2002/0059257 A1 | 5/2002 | Matsumura et al. |
| 2002/0103505 A1 | 8/2002 | Thompson |
| 2002/0161664 A1 | 10/2002 | Shaya et al. |
| 2003/0204415 A1 | 10/2003 | Knowlton |
| 2003/0229514 A2 | 12/2003 | Brown |
| 2006/0007308 A1 | 1/2006 | Ide et al. |
| 2006/0235877 A1* | 10/2006 | Richard ............... G06Q 50/22 |
| 2008/0060652 A1* | 3/2008 | Selvarajan ........... A61M 16/06 128/206.21 |
| 2008/0078396 A1* | 4/2008 | Janbakhsh ........... A61M 16/06 128/205.25 |
| 2008/0112610 A1* | 5/2008 | Israelsen ............... G06T 17/00 382/154 |
| 2008/0312866 A1 | 12/2008 | Shimomura et al. |
| 2009/0267261 A1 | 10/2009 | Mark |
| 2010/0316282 A1 | 12/2010 | Hope |
| 2011/0046915 A1 | 2/2011 | Hol et al. |
| 2011/0282578 A1 | 11/2011 | Miksa et al. |
| 2012/0044476 A1 | 2/2012 | Earhart et al. |
| 2012/0162360 A1 | 6/2012 | Ohtomo et al. |
| 2012/0281087 A1 | 11/2012 | Kruse et al. |
| 2013/0057652 A1 | 3/2013 | Firth |
| 2013/0083964 A1 | 4/2013 | Morris et al. |
| 2013/0088577 A1 | 4/2013 | Hakkarainen et al. |
| 2013/0120736 A1 | 5/2013 | Bosse et al. |
| 2013/0127827 A1 | 5/2013 | Shiell et al. |
| 2013/0155564 A1 | 6/2013 | Schmidt |
| 2013/0215230 A1 | 8/2013 | Miesnieks et al. |
| 2013/0215233 A1* | 8/2013 | Wang ................... H04N 13/239 348/47 |
| 2013/0231892 A1 | 9/2013 | Franke et al. |
| 2013/0286161 A1 | 10/2013 | Lv et al. |
| 2013/0321397 A1 | 12/2013 | Chen et al. |
| 2013/0324875 A1 | 12/2013 | Mestha et al. |
| 2013/0329020 A1 | 12/2013 | Kriveshko et al. |
| 2014/0098018 A1 | 4/2014 | Kim et al. |
| 2014/0104386 A1 | 4/2014 | Shimoyama et al. |
| 2014/0152859 A1 | 6/2014 | Chen |
| 2014/0206443 A1 | 7/2014 | Sharp et al. |
| 2014/0225988 A1 | 8/2014 | Poropat |
| 2014/0278319 A1 | 9/2014 | Thiruvengada et al. |
| 2014/0293220 A1 | 10/2014 | Kornilov et al. |
| 2014/0300538 A1 | 10/2014 | Rijnders |
| 2014/0354830 A1 | 12/2014 | Schafer et al. |
| 2014/0369557 A1 | 12/2014 | Kayombya et al. |
| 2014/0375684 A1 | 12/2014 | Algreatly |
| 2015/0002663 A1 | 1/2015 | Pan et al. |
| 2015/0009277 A1 | 1/2015 | Kuster et al. |
| 2015/0029309 A1 | 1/2015 | Michaeli et al. |
| 2015/0032242 A1 | 1/2015 | Schouwenburg et al. |
| 2015/0145777 A1 | 5/2015 | He |
| 2015/0212343 A1 | 7/2015 | Fonte et al. |
| 2015/0262422 A1 | 9/2015 | Znamenskiy et al. |
| 2015/0265187 A1 | 9/2015 | Bernal et al. |
| 2015/0378433 A1 | 12/2015 | Savastinuk |
| 2016/0085907 A1 | 3/2016 | Schouwenburg et al. |
| 2016/0321420 A1 | 11/2016 | Klee et al. |
| 2017/0203071 A1 | 7/2017 | Lawrenson et al. |
| 2017/0315359 A1 | 11/2017 | Grashow |

FOREIGN PATENT DOCUMENTS

| | | |
|---|---|---|
| DE | 10000790 A1 | 7/2001 |
| JP | 2014077698 A | 5/2014 |
| WO | 2010077380 A2 | 7/2010 |
| WO | 2011076221 A2 | 6/2011 |
| WO | 2013155564 A1 | 10/2013 |
| WO | 2013186160 A1 | 12/2013 |
| WO | 2014057392 A1 | 4/2014 |
| WO | 2014100950 A1 | 7/2014 |
| WO | 2014119997 A1 | 8/2014 |

(56) References Cited

FOREIGN PATENT DOCUMENTS

WO  2014141095 A1  9/2014
WO  2014180657 A2  11/2014

OTHER PUBLICATIONS

Ham, Christopher, et al "Hand Waving Away Scale", Sep. 6, 2014 (Sep. 6, 2014) Network and Parallel Computing; [Lecture Notes in Computer Science; Lect. Notes Computer] Springer International Publishing, Cham, pp. 279-293, XP047296563.
Romdhani, et al.,"Estimating 3D Shape and Texture Using Pixel Intensity, Edges, Specular Highlights, Texture, Constraints and a Prior" Proceedings/2005 IEEE Computer Society Conference on Computer Vision and Pattern Recognition,CVPR 2005:Jun. 20-25, 2005.

* cited by examiner

METHODS AND SYSTEMS FOR PROVIDING INTERFACE COMPONENTS FOR RESPIRATORY THERAPY

CROSS-REFERENCE TO RELATED APPLICATIONS

This application is a continuation of U.S. application Ser. No. 15/344,761, filed on Nov. 7, 2016 which claims the benefit of U.S. Provisional Application No. 62/259,743 filed Nov. 25, 2015, the entire disclosure all of which are hereby incorporated by reference.

1 BACKGROUND OF THE TECHNOLOGY

1.1 Field of the Technology

The present technology relates to methods and systems for manufacturing/sizing patient interfaces, such as masks for respiratory therapy devices, such as by assessing facial details for such masks. More particularly, the technology concerns digital scanning of feature of person's face for such patient interfaces. The present technology also relates to the preparation and design of a patient interface, such as a mask, based on a digital scan of a person's face.

1.2 Description of the Related Art

A range of respiratory disorders exist, e.g., Obstructive Sleep Apnea (OSA), Cheyne-Stokes Respiration (CSR), Obesity Hyperventilation Syndrome (OHS), Chronic Obstructive Pulmonary Disease (COPD), Neuromuscular Disease (NMD), chest wall disorders, etc. These disorders may be characterized by particular events, e.g. apneas, hypopneas, and hyperpneas, and may be treated or prevented using a range of therapies. Such therapies include, for example, Continuous Positive Airway Pressure (CPAP) therapy to treat OSA, and Non-invasive ventilation (NIV) to treat CSR, OHS, COPD, MD and chest wall disorders. These therapies may be provided by a treatment system or device, including respiratory equipment to provide a range of ventilatory support to patients, including full ventilatory support, assisting the patient in taking a full breath, and/or maintaining adequate oxygen levels in the body by doing some or all of the work of breathing.

1.2.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy. FIGS. 1A-1F depict several facial features and anthropomorphic measurements that are subject to variation between individuals. Several of the depicted features are described in greater detail in the glossary below, specifically in the section titled "Anatomy of the Face."

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field

1.2.2 Custom Design of Patient Interface

In order to design a patient interface that provides effective treatment and is comfortable for the user to wear, it is desirable to customize the shape of the patient interface, particularly the mask of the patient interface, to conform with the three-dimensional shape of the user's face. In other to provide such customization, it is often necessary to collect information about the shape of the user's face. This is particularly significant where a seal with the patient's face is necessary for providing an effective respiratory treatment, such as in the application of positive pressure therapy. Moreover, comfort increases patient compliance with therapy.

One way of collecting information about the shape of a user's face is to take a three-dimensional scan of the user's face or head. The three-dimensional scan would include all of the complexities of the user's face. Thus, a patient interface designed based on the three-dimensional scan would be specially designed to conform to the specific contours of the user's face.

A drawback of using a three-dimensional scan is that the equipment used for taking the scan may not be readily available to the user. This means that the user may need to acquire the equipment, which may be expensive. Alternatively, the user may need to schedule an appointment with and travel to a facility that has the equipment. Such scheduling and travel may be inconvenient for the user, and may dissuade the user from obtaining a customized patient interface. Additionally, the user and/or patient interface designer will need to factor the facility's scanning services into the cost of producing the patient interface for the user. Thus, use of three-dimensional scanning technology may add an unwanted cost to the production process. These factors may in turn dissuade the user from ordering a customized patient interface, which in turn (for the reasons explained above) may adversely affect user compliance with therapy or provision of the most effective therapy.

The above drawbacks have been described in the specific context of designing and manufacturing customized patient interfaces and masks, for instance for an individual suffering from a respiratory condition, the same drawbacks and challenges apply to designing and manufacturing any article, apparatus or other apparel that may be worn on a person's head or face. For instance, if a user wishes to order custom-fit sunglasses, goggles, a face mask, or costume, the user may be inconvenienced to have to pay and/or travel in order to have a scan of their face taken.

Accordingly, there is a need for a method and system that collects information about the three-dimensional characteristics of the user's face without the unwanted inconvenience or cost associated with presently known three-dimensional scanning technology and infrastructure.

2 BRIEF SUMMARY OF THE TECHNOLOGY

The present technology is directed towards devices and systems used in the design and production of apparel or other accessories for a user's face, having one or more of improved comfort, cost, efficacy, ease of use and manufacturability.

Some versions of the present technology include an apparatus for acquiring data for generation of a three dimensional facial scan of a user for obtaining a patient respiratory interface component. The apparatus may include an image sensor and lens for capturing two dimensional image data of the user's face. The apparatus may include a motion sensor configured to sense movement data of at least one of a movement of the apparatus and a change in orientation of the apparatus. The apparatus may include a processor configured to receive image data from the image sensor and to receive movement data from the motion sensor, to generate a video file based on the image data received from the image sensor, and to generate a data file based on the movement data received from the motion sensor, and to associate each of the video file and data file with one another. The apparatus may include a transmitter, coupled with the processor, to transmit the associated video and data files to a system comprising a surface engine at a remote destination for generation of a three dimensional representation of the user's face based on the received image data and the received movement data.

In some versions, the image data received at the processor for generating the video file may be captured through a single lens of the apparatus. The motion sensor may include at least one of an accelerometer and a gyrometer. The motion sensor may include an inertial measurement unit (IMU), and wherein the data file may be an IMU file. The apparatus may include a portable housing, wherein each of the image sensor, motion sensor, processor and transmitter is integrated within the portable housing of the apparatus. The transmitter may be a wireless transmitter configured to transmit the video and data files to a remote server over a wireless network. The processor may be configured to play a video file received from the system comprising a surface engine, said video file comprising a three dimensional rendering of the user's face. The apparatus may be a mobile phone of the user.

Some versions of the present technology may include a method for acquiring data with a mobile computing device for generation of a three dimensional facial scan of a user for obtaining a patient respiratory interface component. The method may include controlling an image sensor having a lens to capture two dimensional image data of the user's face. The method may include sensing with a motion sensor configured to sense movement data of at least one of a movement of the image sensor and a change in orientation of the image sensor. The method may include controlling, in a processor configured to receive image data from the image sensor and to receive movement data from the motion sensor, generation of a video file based on the image data received from the image sensor, and generation of a data file based on the movement data received from the motion sensor, and associating each of the video file and data file with one another. The method may include controlling, via a transmitter coupled with the processor, transmission of the associated video and data files to a system comprising a surface engine at a remote destination for generation of a three dimensional representation of the user's face based on the received image data and the received movement data.

Some versions of the present technology may include a computer-readable data storage medium having program instructions encoded thereon configured to cause a processor to perform any of the methods described herein. In some versions, a server may include or have access to such a computer-readable data storage medium. The server may be configured to receive and/or respond to requests for downloading the program instructions of the computer-readable data storage medium to a remote mobile computing device over a network.

Some versions of the present technology may include an electronic system for enrolling an end user for obtaining a patient respiratory interface component. The system may include a customer information subsystem for receiving an enrolment request from an end user device for obtaining a patient respiratory interface component, the enrolment request comprising a unique identifier of the end user. The system may include a three dimensional surface rendering engine, including at least one processor, the three dimensional surface rendering engine configured to render and scale a three dimensional surface of the end user's face based on end-user video frame data, movement data, and the unique identifier of the end user. The system may include a first database for storing said rendered and scaled three dimensional surface, or an identification of the rendered and scaled three dimensional surface, in association with said unique identifier.

In some versions, the customer information subsystem and customer reference database operate on one or more servers in a network. The enrolment request and end-user video frame data and movement data may be received over the network. The three dimensional surface rendering engine is configured to receive timestamp information, wherein the end-user video frame data and movement data are combined at the three dimensional surface rendering engine based on the timestamp information. The three dimensional surface rendering engine may be configured to receive frame selection information designating a preselected subset of the end-user video frame data for use in rendering the three dimensional surface of the end user's face. The frame selection information may include a number of frames selected. The system may include a second database. The first database may store an identification of the rendered and scaled three dimensional surface in association with the unique identifier. The three dimensional surface engine may generate an object file containing said rendered and scaled three dimensional surface and may store the object file, or a reference to the object file, in the second database. The object file, or reference thereto, may be retrieved from the second database based on the identification of said rendered and scaled three dimensional surface in association with said unique identifier. The system may include one or more processors configured to determine one or more dimensions from the rendered and scaled three-dimensional surface for obtaining the patient respiratory interface component. The one or more processors may be configured to compare the one or more dimensions from the rendered and scaled three-dimensional surface with one or more dimensions from one or more respiratory masks.

Some versions of the present technology may include a method of generating a three dimensional surface scan of a user's face for obtaining a patient respiratory interface component. The method may use a mobile device. The method may include receiving video data comprising a plurality of video frames of the user's face taken from a plurality of angles relative to the user's face. The method may include generating a digital three dimensional representation of a surface of the user's face based on the plurality of video frames. The method may include receiving scale estimation data associated with the received video data, the scale estimation data indicative of a relative size of the user's face. The method may include scaling the digital three dimensional representation of the user's face based on the scale estimation data.

In some versions, the plurality of video frames is a subset of the video frames included in the video data. The method may include selecting said plurality of video frames from the video data based on one or more predetermined criteria. The selected plurality of video frames may include at least one front view of the user's face, one left profile of the user's face, and one right profile of the user's face. The three dimensional representation of a surface of the user's face may be generated with a Basel face model, and the method may further include adjusting a three dimensional representation of a surface of a generic face based on data extracted from each frame of the plurality of video frames. The method may include, in each frame of the plurality of video frames, identifying a plurality of points associated with landmark features of the user's face, wherein adjustment of the three dimensional representation of a surface of a generic face may be based on the identified plurality of points. The identifying a plurality of points associated with landmark features of the user's face may be based at least in part on a machine learning algorithm.

In some versions, the method may include, in each frame of the plurality of video frames, identifying a plurality of points associated with landmark features of the user's face; and in each frame of the plurality of video frames, detecting at least one edge of the user's face, wherein generating the three dimensional representation of a surface of the user's face may be based on a combination of the plurality of points and the detected edge of the user's face. The identifying a plurality of points associated with landmark features of the user's face may include: for each of the plurality of video frames, identifying one or more features of the user's face; detecting said landmark features of the user's face based on the identified features; and associating each of the detected landmark features with one or more of the plurality of points. The identifying one or more features further may include using cascade classifiers. The plurality of points comprises at least eighty points. The plurality of points may include at least one hundred thirty two points. At least some of the plurality of points may be representative of the user's eyes, at least some of the plurality of points may be representative of the user's nose, and at least some of the plurality of points may be representative of the user's mouth. At least some of the plurality of points may be representative of an edge of the user's face, wherein the edge of the user's face in a given video frame may be represented by a boundary between the user's face and a background of the video frame. The plurality of points may be subdivided into discrete regions of the user's face, at least one of the discrete regions may be identified in each frame of the plurality of video frames, and wherein the three dimensional representation of a surface of the user's face may be generated based at least in part on said discrete regions. Optionally, each of the user's eyes may be included in a separate discrete region of the user's face. The user's nose may be included in a different discrete region from the user's eyes.

In some versions, the method may include receiving IMU data associated with the received video data. The method may include generating a three dimensional representation of a surface of the user's face based on a combination of the plurality of points, the detected edge of the user's face, and the received IMU data. The method may include correlating the received IMU data with respective video frames of the received video data. The scale estimation data may include the received IMU data. The scale estimation data may include an interpupil distance of the user's face. The scale estimation data may include a measurement of an article placed on the user's face and having a predetermined size or shape. The scale estimation data may include information from one or more signals transmitted from a transmitter positioned at the user's face. The scale estimation data may include a manually input measurement relating to a scale factor of the user's face. The received video data may be collected by two or more mobile devices, and wherein the scale estimation data may include a measurement relating to a distance between at least two of the mobile devices. The received video data may be collected by two or more mobile devices mounted to a helmet worn by the user, and wherein the scale estimation data may be a predetermined value based on a fixed distance of the two or more devices from the user's face. The scale estimation data comprises a measurement of a distance between the mobile device and the user's face based on an adjustable focus property of the mobile device. The scale estimation data may include a time delay measured by an ultrasonic or electromagnetic measuring device. The scale estimation data comprises a measurement of a structured light emitted by one or more flash bulbs of the mobile device.

Some versions of the present technology may include a computer-readable data storage medium having program instructions encoded thereon configured to cause a processor to perform a method of generating a three dimensional surface scan of a user's face for obtaining a patient respiratory interface component such as by any of the described methods herein. Some versions of the present technology may include a computer-readable data storage medium having a file encoded thereon, the file encoding a representation of a three dimensional surface of a user's face, the representation being generated using any of the described methods herein.

Some versions of the present technology may include a system for generating a three dimensional surface scan of a user's face for obtaining a patient respiratory interface component. The system may include one or more servers, the one or more servers may include one or more processors. The one or more processors may be configured to perform any of the methods described herein.

Some versions of the present technology may include system for obtaining a patient respiratory interface component. The system may include one or more data stores storing a training dataset of three dimensional surfaces, each three dimensional surface representative of a surface of a human face. The system may include one or more processors configured to receive a plurality of two dimensional images of a face of a human subject, each of the images having been taken at an unspecified distance from and an unspecified angle relative to the human subject. The system may include one or more processors configured to receive a request to generate a new three dimensional surface from said images of the face of the human subject. The system may include one or more processors configured to generate the new three dimensional surface based on a support vector machine and said images, wherein the support vector machine may be derived from the training dataset of three dimensional surfaces.

In some version, the plurality of two dimensional images may include at least one front profile of the human subject, and wherein the one or more processors are further provided for scaling the generated new three dimensional surface based on information derived from the front profile. The one or more processors may be configured to receive an inertial measurement dataset, and to generate the new three dimensional surface based on said inertial measurement dataset. The one or more processors may be configured to scale the generated new three dimensional surface based on said inertial measurement dataset. The one or more processors may be configured to receive time information associated with the two dimensional images, and to generate the new three dimensional surface based on said time information. The one or more processors may be configured to receive the plurality of two dimensional images and the request from a mobile apparatus of the human subject. The generated new three dimensional surface may include a grid superimposed over a representation of the face of the human subject. Each of the plurality of two dimensional images received by the one or more processors may be taken from a single lens. Optionally, the system may be configured to identify or facilitate construction of the patient respiratory interface component based on the generated new three-dimensional surface.

Some versions of the present technology may include a method for obtaining a patient respiratory interface component. The method may include accessing, in one or more data stores, a training dataset of three dimensional surfaces, each three dimensional surface representative of a surface of a human face. The method may include, in one or more processors, receiving a plurality of two dimensional images of a face of a human subject, each of said images having been taken at an unspecified distance from and an unspecified angle relative to the human subject. The method may include, in one or more processors, receiving a request to generate a new three dimensional surface from said images of the face of the human subject. The method may include, in one or more processors, generating the new three dimensional surface based on a support vector machine and said images, wherein the support vector machine may be derived from the training dataset of three dimensional surfaces. Some versions of the present technology may include a computer-readable data storage medium having program instructions encoded thereon configured to cause a processor to perform such a method.

Some versions of the present technology may include a method for obtaining a patient respiratory interface component for a user's face. The method may include receiving video data from the user, the video data including a video scan of the user's face. The method may include determining one or more anthropometric measurements based on information derived from the video scan. The method may include generating a three dimensional representation of the user's face based on the determined one or more anthropometric measurements. The method may include scaling the three dimensional representation of the user's face. The method may include obtaining the patient respiratory interface component based on the scaled three dimensional representation of the user's face, wherein the determined one or more anthropometric measurements may be made using a processor and may have an accuracy of at least about ±3 mm when scaled. The one or more anthropometric measurements may include at least one of: an alar angle, a nasolabial angle and a nose width. The one or more anthropometric measurements may include at least one of a mouth width and an upper lip height. Said determinations of anthropometric measurements may have an accuracy of at least about ±0.5 mm when scaled. Some versions of the present technology may include a system for obtaining a patient respiratory interface component for a user's face, including one or more processors, such as one or more processors configured to perform any of such method(s). Some versions of the present technology may include a computer-readable data storage medium having program instructions encoded thereon configured to cause one or more processors to perform a any of such method(s).

Some versions of the technology may include an apparatus for acquiring data for construction of a three-dimensional facial scan of a user. The apparatus may include an image sensor and lens for capturing two dimensional image data of the user's face. The apparatus may include a motion sensor configured to sense movement data of at least one of a movement of the apparatus and a change in orientation of the apparatus. The apparatus may include a processor. The processor may be configured to receive image data from the image sensor, to receive movement data from the motion sensor, to generate a video file based on the image data received from the image sensor, to generate a data file based on the movement data received from the motion sensor, and to associate each of the video file and data file with one another. The apparatus may include a transmitter, coupled with the processor, to transmit the associated video and data files to a system. The system may include a surface engine at a remote destination for construction of a three-dimensional representation of the user's face based on the received image data and the received movement data.

In some versions, the image data may be captured through a single lens of the apparatus. The motion sensor may include at least one of an accelerometer and a gyrometer. Optionally, the motion sensor may include an inertial measurement unit (IMU), such that the data file is an IMU file. The apparatus may include a portable housing. Each of the image sensor, motion sensor, processor and transmitter may be integrated within the portable housing. The transmitter may be a wireless transmitter capable of transmitting the video and data files to a remote server over a wireless network. The processor may be configured to play a video file received from the system. The video file may include a three-dimensional rendering of the user's face. The apparatus may be a mobile phone.

Some versions of the present technology may include an electronic system for enrolling an end-user for production of a customized patient interface component. The system may include a customer information subsystem for receiving an enrolment request from an end-user device. The enrolment request may include a unique identifier of the end-user. The system may include a three-dimensional surface engine, including at least one processor. The three-dimensional surface engine may be configured to render and scale a three-dimensional surface of the end-user's face based on a customized patient interface component request. The customized patient interface component request may include video frame data, movement data, and the unique identifier of the end-user. The system may include a first database for storing the rendered and scaled three-dimensional surface (or an identification of the rendered three-dimensional surface) in association with the unique identifier.

In some versions, the customer information subsystem and customer reference database may be stored on one or more servers in a network, such that the enrolment request and customized patient interface component request may be received over the network. The customized patient interface component request may include timestamp information. The video frame data and movement data may be combined at the three-dimensional surface engine based on the timestamp information. The customized patient interface component request may include frame selection information designating a pre-selected subset of the video frame data for use in rendering the three-dimensional surface of the end-user's face. The customized patient interface component request may indicate a number of frames selected. Optionally, the electronic system may include a second database. The first database may store an identification of the rendered three-dimensional surface in association with the unique identifier. The three-dimensional surface engine may generate an object file containing the rendered three-dimensional surface, and may store the object file (or a reference to the object file) in the second database. The object file (or reference thereto) may be retrieved from the second database based on the identification of the rendered three-dimensional surface in association with the unique identifier.

Some versions of the present technology may include a method of generating a three-dimensional surface scan of a user's face using a mobile device. The method may involve receiving video data including a plurality of video frames of the user's face taken from a plurality of angles relative to the user's face. The method may involve generating a digital three-dimensional representation of a surface of the user's face based on the plurality of video frames. The method may involve receiving scale estimation data associated with the received video data. The scale estimation data may be indicative of a relative size of the user's face. The method may involve scaling the digital three-dimensional representation of the user's face based on the scale estimation data.

In some versions, the plurality of video frames may be a subset of the video frames included in the video data. The plurality of video frames may be selected from the video data based on one or more predetermined criteria. The selected video frames may include at least one front view of the user's face, one left profile of the user's face, and one right profile of the user's face. Optionally, the three-dimensional representation of a surface of the user's face may be generated with a Basel face model. A three-dimensional representation of a surface of a generic face may be adjusted based on data extracted from each frame of the plurality of video frames.

The method may involve, for each frame of the plurality of video frames, identifying a plurality of points associated with landmark features of the user's face. The identifying may be based at least in part on a machine learning algorithm. The identifying may involve using cascade classifiers (e.g., Haar feature-based cascade classifiers). Adjustment of the three-dimensional representation of a surface of a generic face may be based on the identified plurality of points. The method may involve, detecting at least one edge of the user's face. Generating the three-dimensional representation of a surface of the user's face may be based on a combination of the plurality of points and the detected edge of the user's face. Features of the user's face may be identified based on the points, and landmark features may be identified based on those features. Each of the detected landmark features may be associated with one or more of the plurality of points.

In some versions, the plurality of points may include at least 80 points, or at least 132 points. At least some of the points may be representative of the user's eyes, nose, and/or mouth. At least some of the points may be representative of an edge of the user's face (e.g., a boundary between the user's face and a background of a given video frame). The points may be subdivided into discrete regions of the user's face. At least one discrete region may be identified in each video frame. The three-dimensional representation of a surface of the user's face may be generated based at least in part on the discrete regions. Each of the user's eyes may be included in a separate discrete region. The user's nose may be included in a different discrete region from the user's eyes.

The method may optionally involve receiving IMU data associated with the received video data, and generating a three-dimensional representation of a surface of the user's face based on a combination of the plurality of points, the detected edge of the user's face, and the received IMU data. The method may involve correlating the received IMU data with respective video frames of the received video data. The scale estimation data may include the IMU data, an inter-pupil distance of the user's face, a measurement of an article placed on the user's face and having a predetermined size or shape, information from one or more signals transmitted from a transmitter positioned at the user's face, a manually input measurement relating to a scale factor of the user's face, a measurement of a distance between the mobile device and the user's face based on an adjustable focus property of the mobile device, a time delay measured by an ultrasonic or electromagnetic measuring device, and/or a measurement of a structured light emitted by one or more flash bulbs of the mobile device.

In some versions, the received video data may be collected by two or more mobile devices. The scale estimation data may include a measurement relating to a distance between at least two of the mobile devices. The devices may be mounted to a helmet worn by the user, such that scale estimation data may be a predetermined value based on a fixed distance of the devices from the user's face.

Some versions of the present technology may include a computer-readable memory storage medium having program instructions encoded thereon configured to cause a processor to perform a method of generating a three-dimensional surface scan of a user's face, the method including any one of the methods described herein.

Some versions of the present technology may include a computer-readable memory storage medium having a file encoded thereon. The file may encode a representation of a three-dimensional surface of a user's face generated using any one of the methods described herein.

Some versions of the present technology may include a system. The system may include one or more data stores storing a training dataset of three-dimensional surfaces. Each three-dimensional surface may be representative of a surface of a human face. The system may include one or more processors configured to receive a plurality of two-dimensional images of a subject. Each of the images may have been taken at an unspecified distance from and an unspecified angle relative to the subject. The one or more processor may be configured to receive a request to generate a new three-dimensional surface from said images, and to generate the new three-dimensional surface based on a support vector machine. The support vector machine may be derived from the training dataset of three-dimensional surfaces.

In some versions, the plurality of two-dimensional images may include at least one front profile of the subject. The one or more processors may be provided for scaling the new three-dimensional surface based on information derived from the front profile. The one or more processors may be configured to receive an inertial measurement dataset, and a request to generate a new three-dimensional surface from the images and the inertial measurement dataset. The processors may be configured to scale the new three-dimensional surface based on the inertial measurement dataset. The processors may be configured to receive time information associated with the two-dimensional images, and a request to generate a new three-dimensional surface from the images and time information. The plurality of two-dimensional images and the request may be received from a mobile apparatus of the subject. The generated three-dimensional surface may include a grid superimposed over the representation of the user's face. Each of the two-dimensional images may be taken from a single lens.

Some versions of the present technology may include a method of designing a custom-fit article for a user's face. The method may involve receiving video data from the user. The video data may include a video scan of the user's face. The method may involve determining one or more anthropometric measurements based on information derived from the video scan. The method may involve generating a three-dimensional representation of the user's face based on the determined one or more anthropometric measurements. The method may involve scaling the three-dimensional representation of the user's face. The method may involve designing the custom-fit article based on the scaled three-dimensional representation of the user's face. The determined one or more anthropometric measurements may be made using a processor, and may have an accuracy of at least about ±3 mm when scaled.

In some versions, the one or more anthropometric measurements may include an alar angle, a nasolabial angle, a nose width, a mouth width, and/or an upper lip height. Determinations of anthropometric measurements may have an accuracy of at least about ±0.5 mm when scaled.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

2.1 SYSTEM ARCHITECTURE

Examples of the systems outlined herein may be configured to collect information about the three-dimensional characteristics of the user's face, prepare a digital representation of the three-dimensional characteristics of the user's face, obtain a patient interface (e.g., a respiratory mask) for the user based on such a digital representation, enroll the user in a program for designing a custom-fit patient interface (e.g., custom respiratory mask), select a suitable size patient interface (e.g., off-the-shelf respiratory mask) for the user based on such a digital representation or any combination of the above. The system may operate based on information provided from an end-user device of the user, such as information input by the user into an input device, as well as information gathered by the device's sensors. The system may also include one or more other computing devices, such as one or more servers, with one or more processor(s) programmed or configured to perform the three-dimensional rendering functionalities described in this specification.

As a whole, the system may be configured to collect data for—and process—a three-dimensional scan of the user's face, based at least in part on two-dimensional data (e.g., standard video frames) gathered from the user's own personal device, such as a smart phone, or other mobile device equipped with a camera lens and video recording capabilities. In this regard, the user does not need to be inconvenienced to acquire an expensive three-dimensional scanning apparatus, or to visit a facility that uses a three-dimensional scanning apparatus, since the information needed to construct a three-dimensional facial scan may be collected from an apparatus that the user already owns and regularly has available to themselves.

Figure 1A:
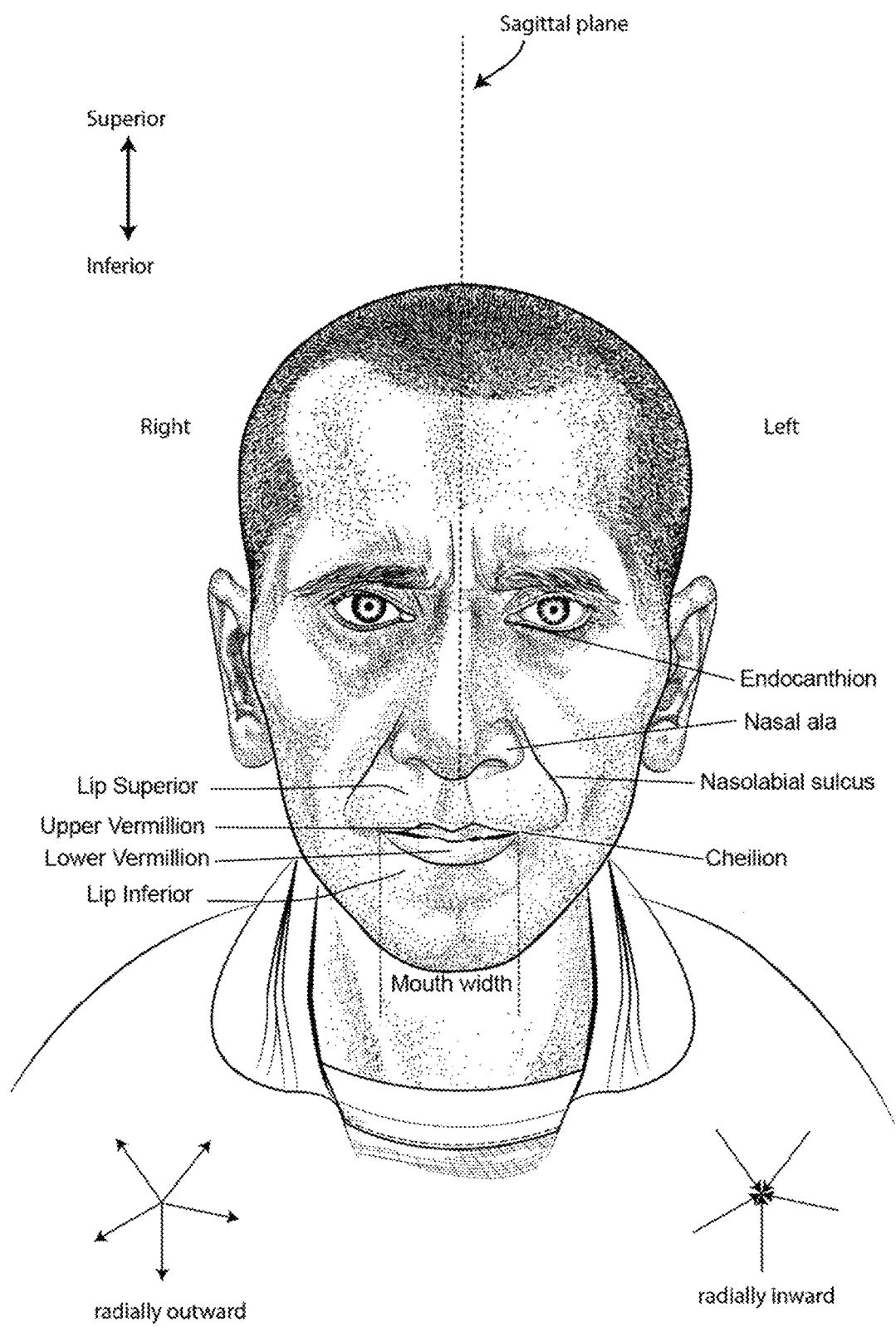
FIG. 1A is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 1B:
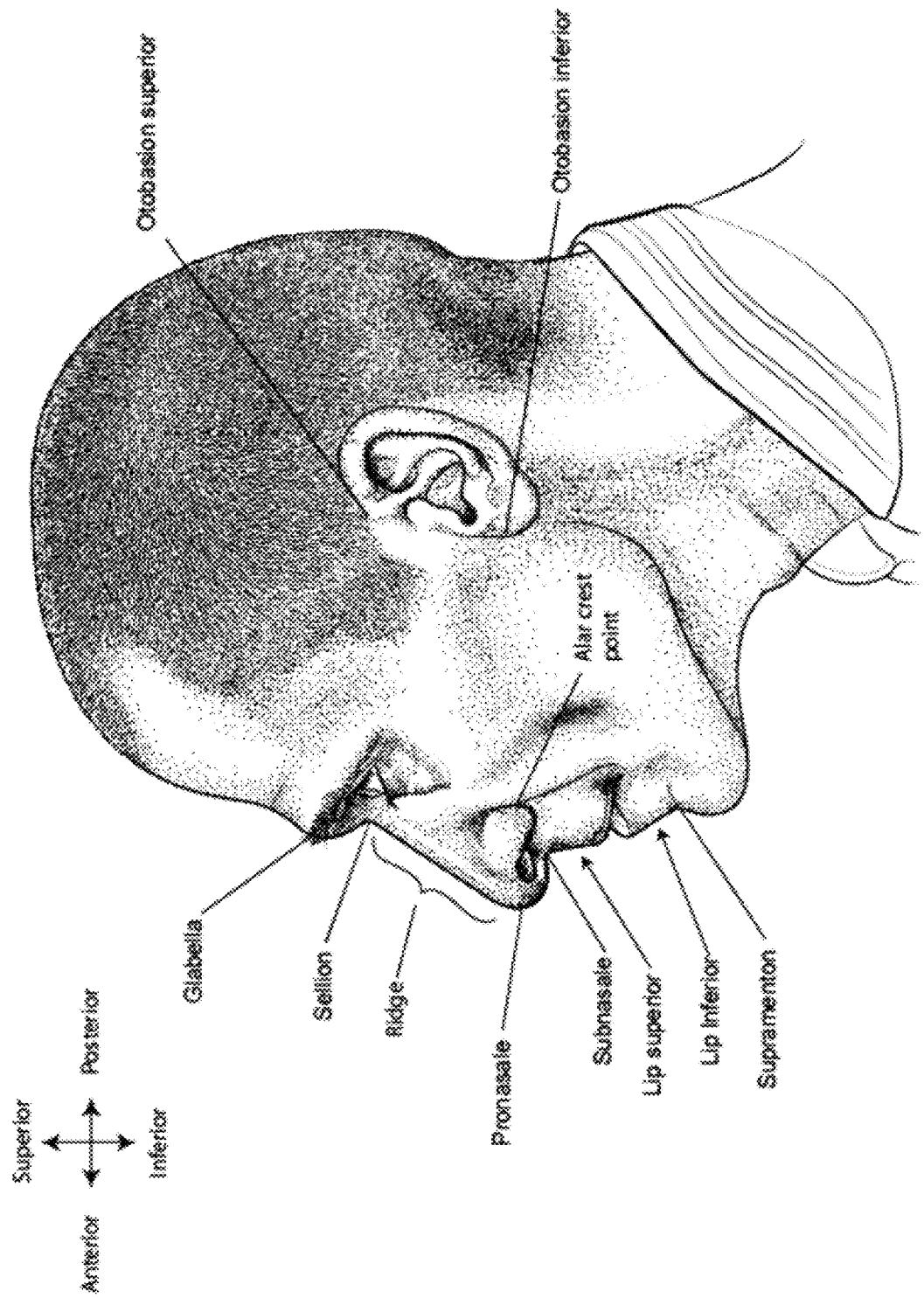
FIG. 1B is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 1C:
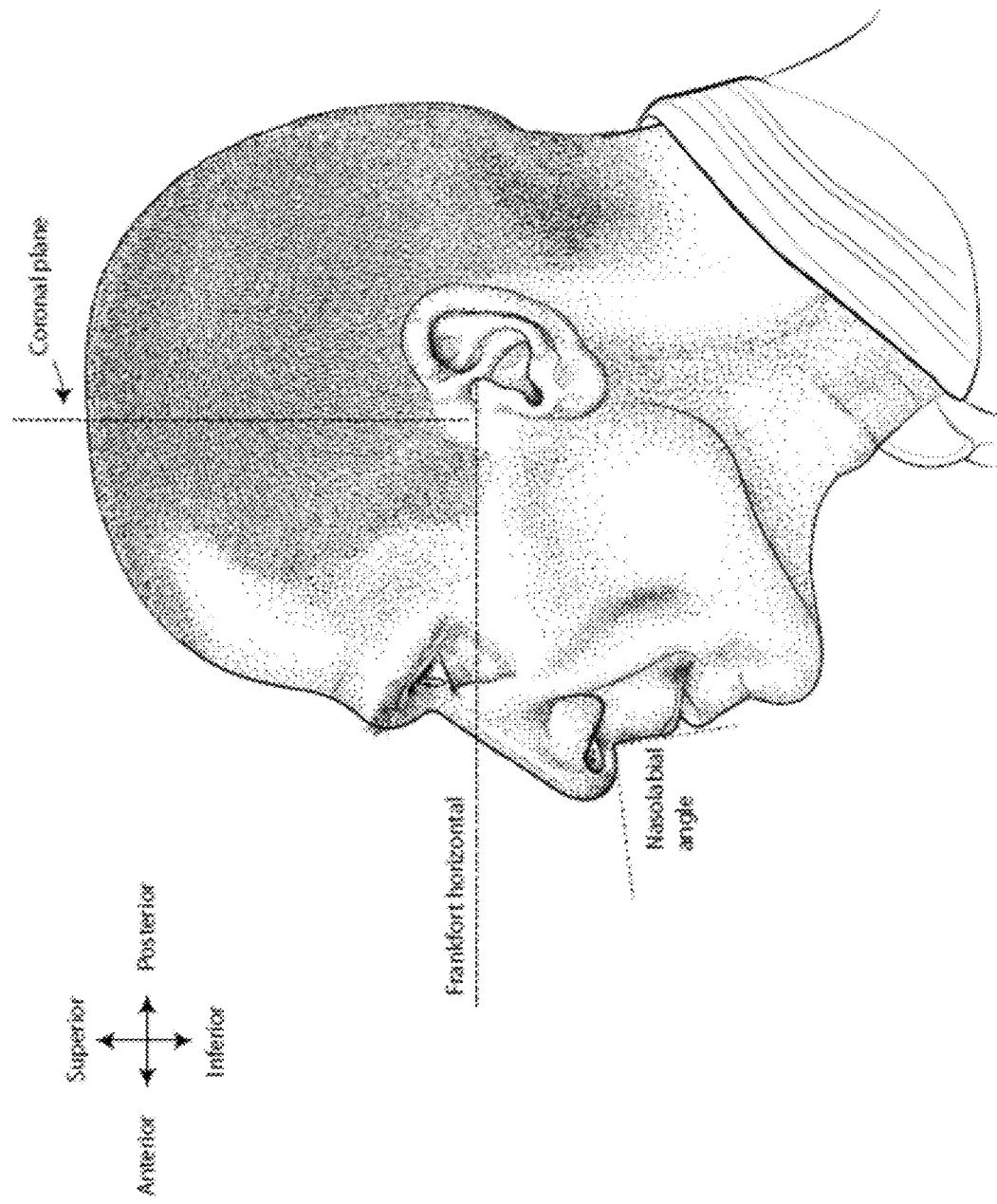
FIG. 1C is a further side view of a head. The approximate locations of the Frankfort horizontal and nasolabial angle are indicated. The coronal plane is also indicated.
Figure 1D:
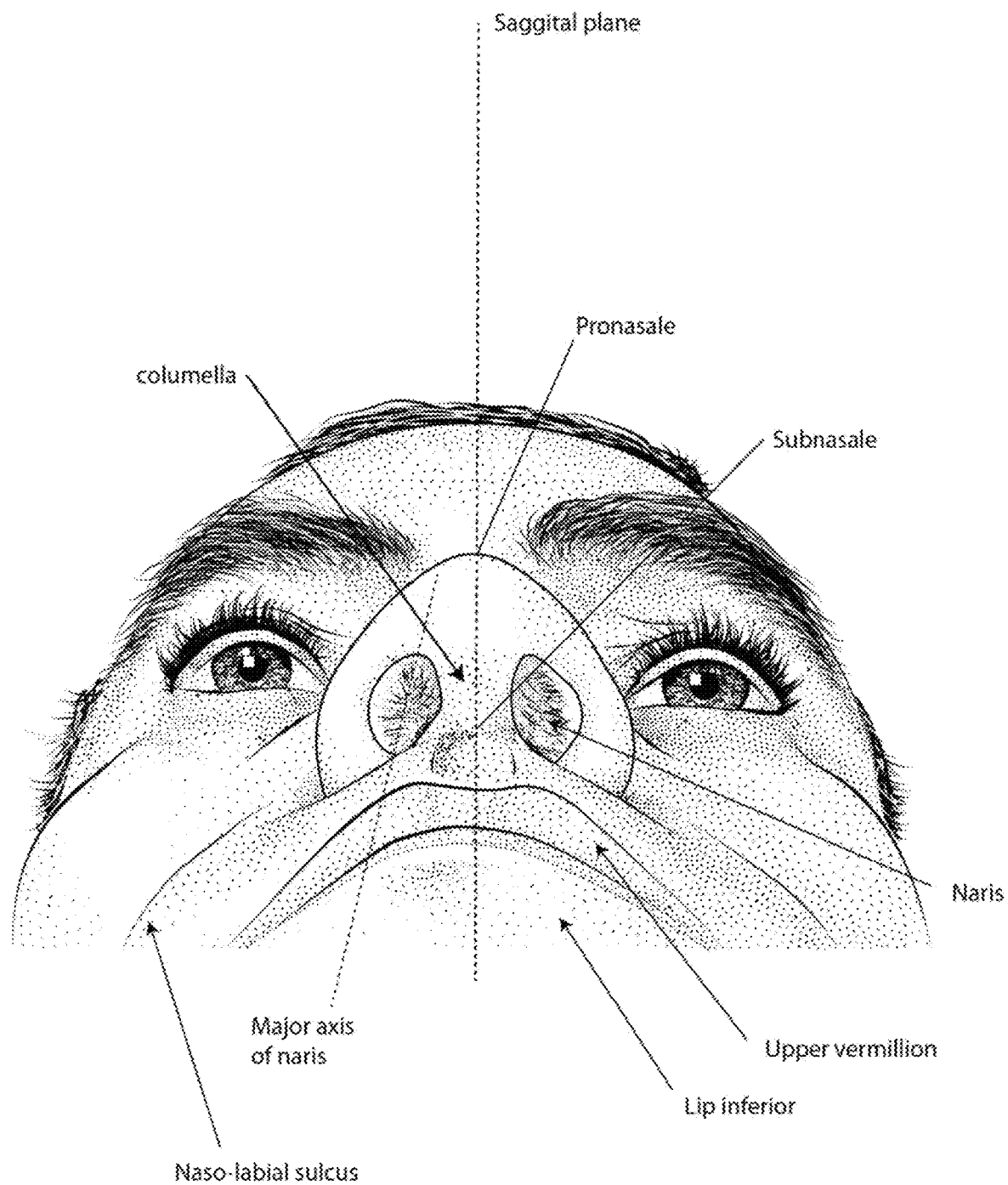
FIG. 1D shows a base view of a nose with several features identified including naso-labial sulcus, lip inferior, upper Vermilion, naris, subnasale, columella, pronasale, the major axis of a naris and the sagittal plane.
Figures 1E, 1F:
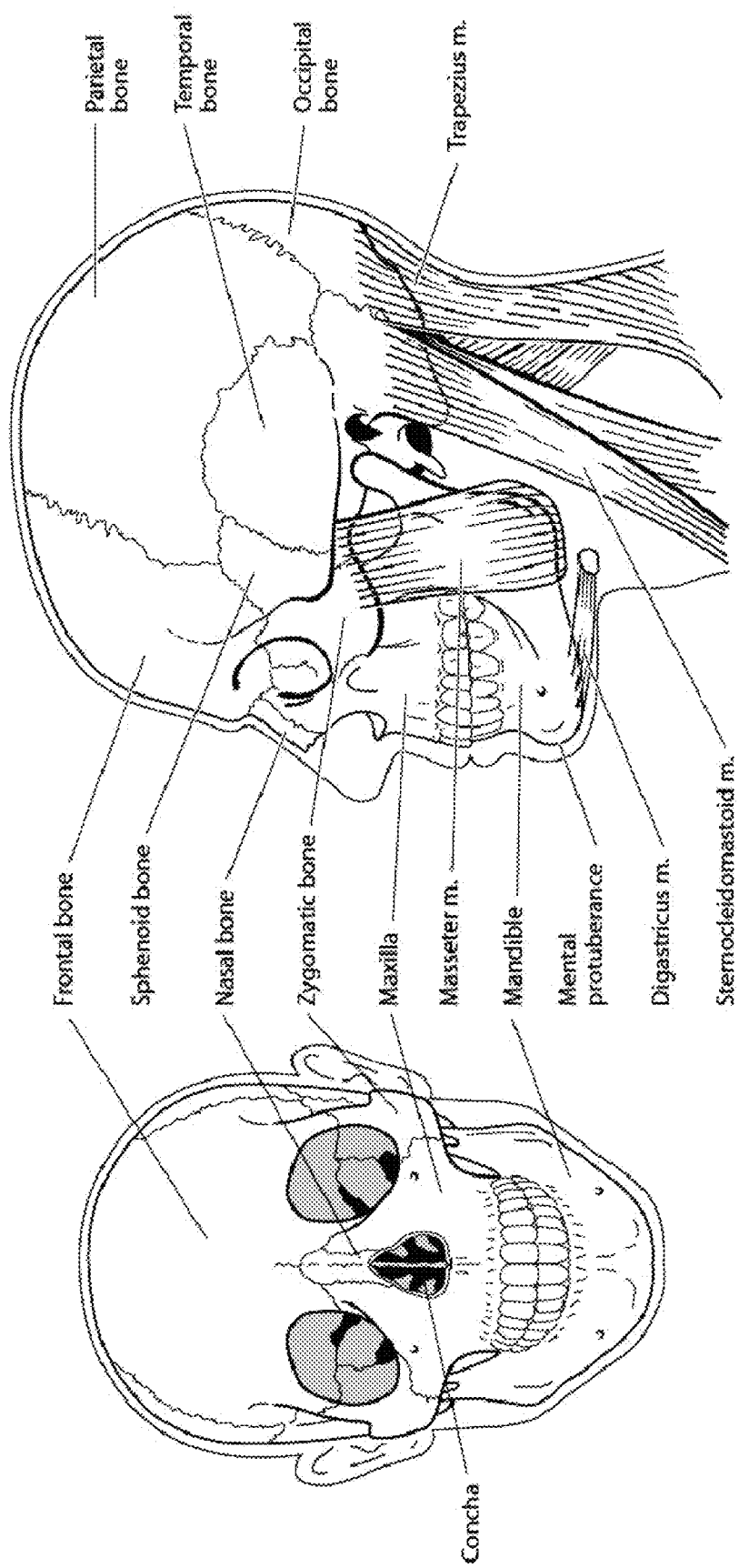
FIG. 1E shows a front view of the bones of a skull including the frontal, nasal and zygomatic bones. Nasal concha are indicated, as are the maxilla, and mandible.
FIG. 1F shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.
Figure 2:
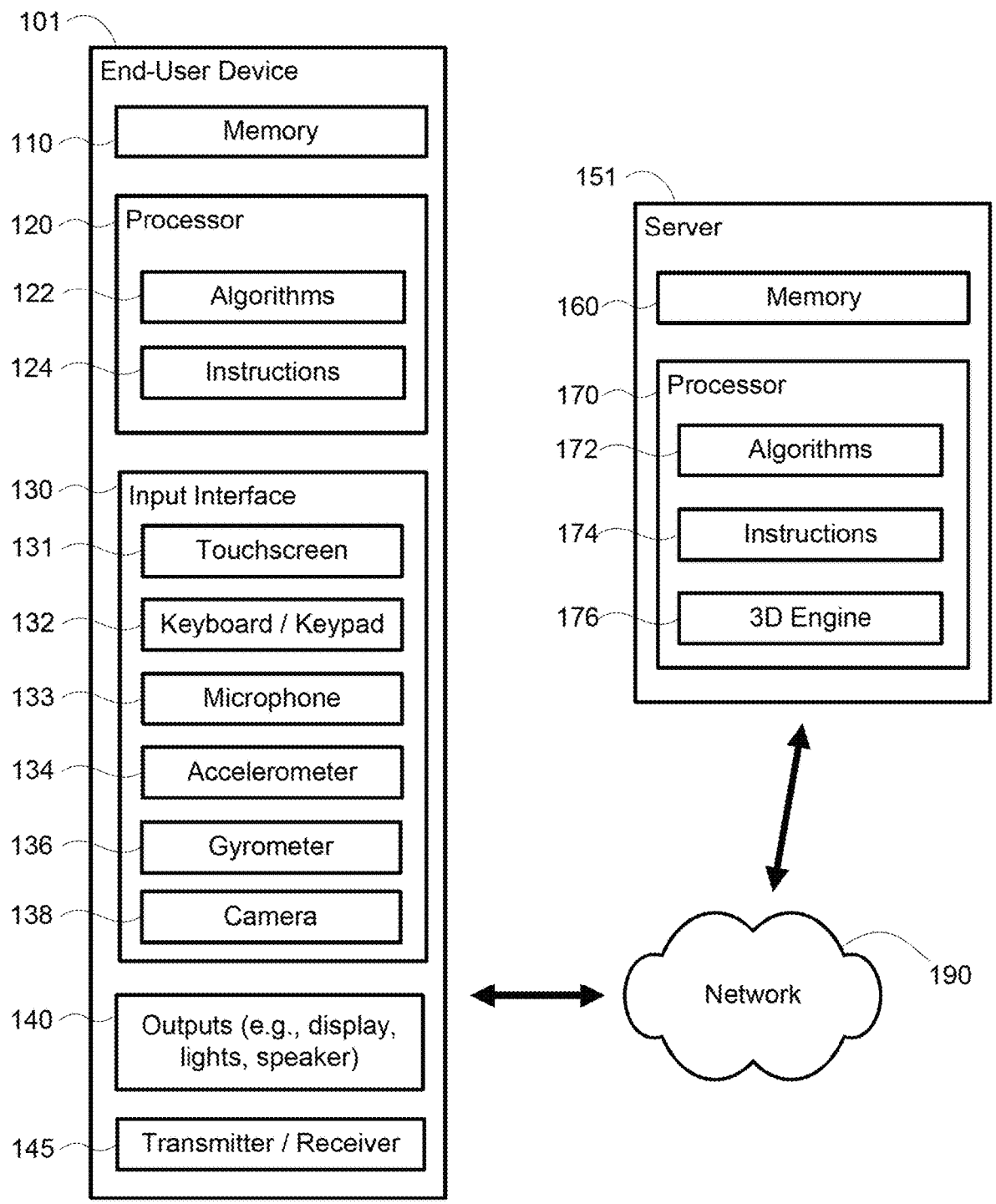
FIG. 2 shows an example system having an end-user device, such as a mobile device, and a server, in accordance with one form of the present technology.

FIG. 2 shows an example system 100 including an end-user device 101 and a server 151. The end-user device 101 may be communicatively coupled with the server 151 such that information may be transmitted from one to the other, or vice versa. Such transmission may be conducted via a wired and/or wireless network 190 connection (e.g., Ethernet, optical fibre, CDMA, GSM, LTE, WiFi, Bluetooth, etc.) Although only one end-user device and only one server are shown in FIG. 2 for illustrative purposes, the system 101 may include numerous other end-user devices and/or may include a network of servers as well as multiple server-end processing devices in communication with the server(s) and, thereby, the end-user device(s).

The end-user device 101 may include a memory 110 and processor 120, which itself may contain algorithms 122 for performing any of the end-user device based operations described throughout this specification, as well as instructions 124 for carrying out any of the end-user device based functions described throughout this specification.

The end-user device may also include an input interface 130 including user input devices such as a touch screen 131, keyboard or keypad 132, microphone 133, etc., capable of receiving instructions and other information from the user. The input interface 130 may also include one or more motion sensors, such as an accelerometer 134, gyrometer 136, or other inertial measurement unit (IMU) capable of determining spatial translation, orientation, momentum, angular momentum, and/or other indicator of a motion (also termed "IMU data" herein) of the end-user device 101. The motion sensors may be built-in to the device, or may be attached to the device peripherally. The input interface 130 may also include at least one camera 138, including include one or more image sensors and lenses, for capturing video information about a user's face. The camera 138 may be built-in to the device 101, or may be attached to the device 101 peripherally. In those cases in which motion data is utilized to construct a three-dimensional representation of the user's face, the camera 138 should be integrated with the accelerometer 134 and/or gyrometer 136 such that those sensors are capable of detecting changes in motion and/or orientation of the camera 138.

The end-user device 101 may be equipped with a single lens and image sensor array through which video may be collected. The individual frames of such a video, by virtue of the single lens through which they are captured, are limited to being two-dimensional representations of the captured subject. The distance from which the individual frames of the video data were captured may be unspecified and unknown. Additionally, the angle from which the frames were taken, relative to the subject of the frames (e.g., the user), may also be unspecified and unknown. Nonetheless, such video data (and thus such built-in camera equipment) may still be sufficient for reconstructing a three-dimensional surface representative of the user's face when carrying out the methods described in this specification.

The end-user device may also include one or more output interfaces 140 (e.g., a display, vibrator, speaker, LED or other light, etc.) capable of outputting information and instructions to the user, such as an alert (e.g., success or failure of a transmission or transaction) or an instruction (e.g., to take a video scan, to calibrate the end-user device, etc.). The end-user device may also contain a transmitter/receiver 145 for transmitting data to and/or receiving data from the server 151. The transmitter/receiver 145 may be a wireless transmitter/receiver capable of transmitting video and data files over the wireless network 190.

The end-user device 101 may include a portable housing, such that each of the image sensor(s), motion sensor(s), the processor and transmitter/receiver may be carried by a user along with the device's housing.

In the examples of this specification, the end-user device is a movable device that collects motion data and may, for example, be a smart-device, such as a smart-phone, tablet computer or smart-watch, or other device capable of being carried by the user while taking a video. In the example of such smart devices, the image sensor(s), motion sensor(s), processor and transmitter/receiver may be integrated with the portable housing of the device. The end-user device 101 may be configured to download program instructions for its processor(s), such as for implementing the methods described in more detail herein, from a server on a network where the server stores such programming instructions in an electronic information storage medium for access on the network.

Turning next to the server 151, the server may also include a memory 160 and processor 170, which itself may contain algorithms 172 for performing any of the server-end operations described throughout this specification, as well as instructions 174 for carrying out any of the server-end functions described throughout this specification. The processor 170 may also include hardware, or access software from memory, for a three-dimensional rendering engine 176 for rendering a three-dimensional surface representative of the user's face based on data collected at, and received from, the end-user device 101.

Figure 3:
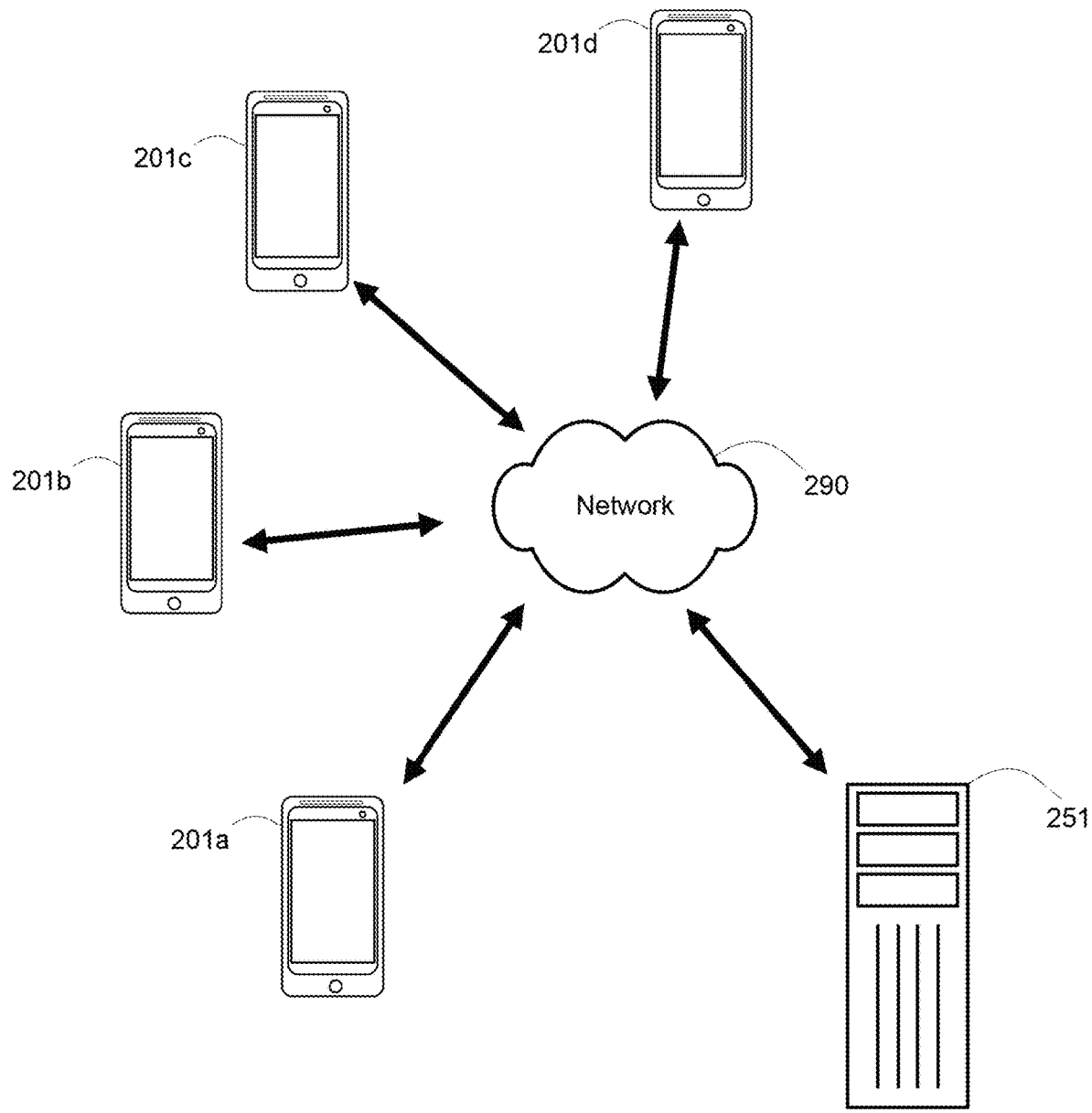
FIG. 3 shows an example system having multiple end-user devices and a server, in accordance with one form of the present technology.

The server 151 also, as with the end-user device, includes hardware and/or software by which the server 151 is capable of connecting to a network over which data may be received from or transmitted to the end-user device 101, as well as to other end-user devices. For instance, FIG. 3 shows an example arrangement in which a server 251 (which may be comparable to the server 151 of FIG. 2) is connected over a wireless network 290 to several mobile end-user devices 201*a-d*.

Although the server in FIG. 2 is shown only to include memory, the server 151 may further be capable of accessing other external memories, data stores, or databases (not shown). For example, information processed at the server 151 may be sent to an external data store (or database) to be stored, or may be accessed by the server 151 from the external data store (or database) for further processing. Additionally, the system 100 may include multiple such data stores and/or databases. In some cases, the data stores or databases may be separately accessible, such as each being accessible to a different server (e.g., a user identification database accessible to one server of the network, and a three-dimensional surface database accessible to a second server of the network). In other cases, the data stores or databases described herein may not necessarily be separate, but may be stored together but as part of separate files, folders, columns of a table in a common file, etc.

In the example of FIG. 2, the server 151 is assigned the task of rendering the three-dimensional surface based on the information collected at the end-user device 101. The purpose of this arrangement is at least in part to relieve the end-user device 101 of performing the processing and carrying the hardware and/or software necessary to perform such rendering. In this regard, the user does not have to purchase such hardware or software, or a device with a processor capable of performing such functions. Instead the user can merely transmit the data from their device 101 to some external location for processing. In this regard, the present disclosure is not limited in terms of any particular server/processor arrangement. Rather, what is intended by the arrangement of FIG. 2 is to demonstrate one example system which provides the benefit of rendering the three-dimensional surface using devices external to the end-user device 101. Nonetheless, in other examples of the disclosure, if the end-user device 101 is properly equipped and contains enough processing power, the three-dimensional rendering hardware/software, may be included with the end-user device 101.

2.2 THREE-DIMENSIONAL FACIAL SCAN USING END-USER DEVICE

In one example of this specification, the data for constructing a three-dimensional surface of the user's face may be collected by the user taking a video—or having another person take a video—of themselves using the built-in camera of their smart-phone, other mobile device, or other appropriately equipped end-user device. Taking a video may involve holding the camera at a distance from the user's face and the user turning their head side to side so that the camera captures various profiles of the user's face from various angles. Such profiles may include a front profile, side (left and right profiles), and other intermediary angles. Taking the video may further involve the user tilting their head up and down to capture additional profiles, and thus additional information about their facial contours and complexities, such as the underside of their nose. Alternatively, instead of the user turning and tilting their head, the camera may be panned around the user's face, thus collecting profiles of the user's face from the same various angles.

An additional video of the user's face may be taken in order to calibrate the information gathered from the first video. Taking this additional video may involve moving the camera close to and then away from their face. Preferably, the user will keep their head still for this video, so that the size of the user's head (or face) may be determined from the change in size of the user's head (or face), as imaged, as the camera moves towards and away from the user. Simply speaking, this additional video may provide information about the size of the user's head that is not necessarily available from the first video. It may also be used to calculate a scaling factor.

Figure 4:
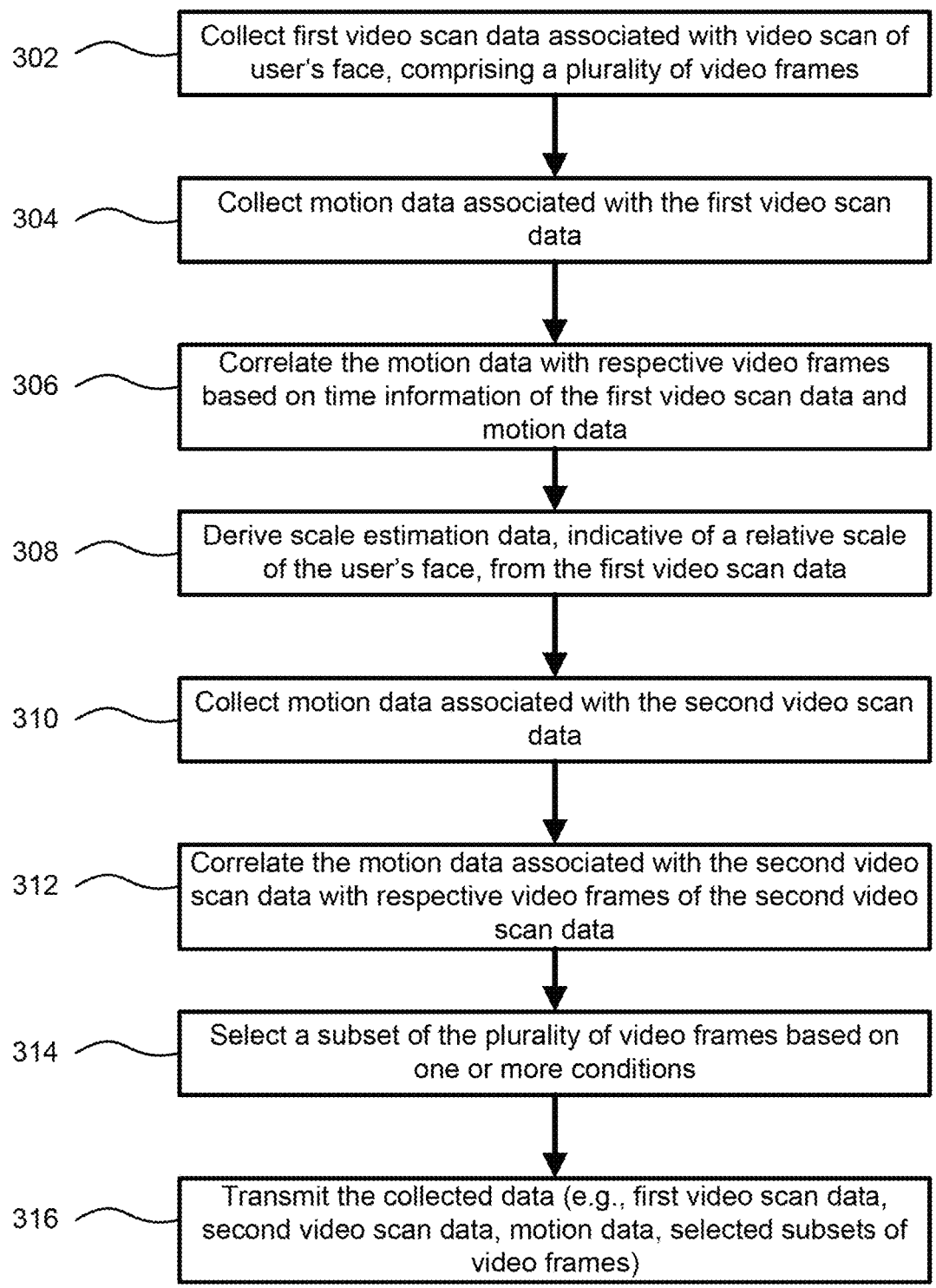
FIG. 4 shows a method of collecting facial scan data using an end-user device in accordance with one form of the present technology.

FIG. 4 is a flow diagram of an example method 300 for an end-user device (e.g., in the example of FIG. 2, end-user device 101), such as a smart-phone or tablet computer, to collect and transmit data sufficient for rendering a three-dimensional facial scan of the user. In FIG. 4, the end-user device collects various data using its inputs and sensors, performs some processing steps on the data, and then sends the partially processed data out (e.g., in the example of FIG. 2, to server 151 of system 100) for further processing (e.g., three-dimensional rendering).

The device collects video data from a first video scan of the user's face (at 302). The video data may include a plurality of video frames. The video frames may be taken from a plurality of angles relative to the user's face, and those angles may provide various profiles of the user's face. By collecting a video scan, as compared to taking several photographs of the user's face from various angles, the video frames may be sequenced, such that identifiable landmark features of the user's face may be tracked frame-by-frame along the sequence of video frames. The video scan data may be collected by one or more image sensors and received by the device's processor, where a video file may be generated based on the video scan data.

At 304, the device may optionally collect motion data (e.g., IMU data) during the first video scan. The motion data may include inertial measurements, such as indicating a change in motion or orientation of the device, during the first video scan. While it is not required that the user move the device during the first video scan, and may in fact be preferred that the user not move the device, the user may be holding the device in their hand during the video scan and thus, in the natural course of turning and tilting their head, may unknowingly or inadvertently move or tilt the device. Thus, collecting the motion data during the first video scan can help to stabilize the video information collected during the scan by indicating a change in the point of reference, or angle of reference, of the scanned video data.

The motion data may be collected by the one or more motion sensors of the device, and like the video scan data, may also be provided to the device's processor, where a data file (optionally a text file) may be generated based on the motion data. In the case of motion data collected by an IMU, the data file may be an IMU file in plain text format.

The motion data may be correlated to the video scan data (e.g., mapped temporally over the duration of the video scan) at this stage (e.g., on the end-user device end) or a later stage (e.g., at a remote location) of processing (at 306). For instance, each of the video frames of the video scan data may be assigned a timestamp, and the motion data collected over time may similarly be assigned timestamps. In addition to the timestamps, an amount of delay between collection of the motion data and the video data may be known, and such delay may be factored into the timestamps in order to synchronize the motion and video data. Thus, the video scan and motion data may be correlated based on their respective time information (e.g., timestamps, time delay information). The correlated motion data may then be used to correct or compensate the collected video scan data, effectively creating a video scan taken from a single point and/or angle of reference.

In those examples in which the user were to pan the device around their face instead of turning and tilting their face, correlating motion data to the video scan data may be similarly useful to indicate whether the distance or angle of the camera changed during the scan. For example, if the camera were held closer to the user during a scan of the user's left profile than during a scan of the user's right profile, the video scan data may suggest that the left ear of the user is larger than the right ear. Thus, by collecting motion data, assuming that the user's face remained still during the video scan, it can be determined that, and how much, the camera moved away from the user's face from the left profile scan to the right profile scan, and the profiles may be corrected or compensated to yield a more accurate representation of the user's face.

Figure 5A:
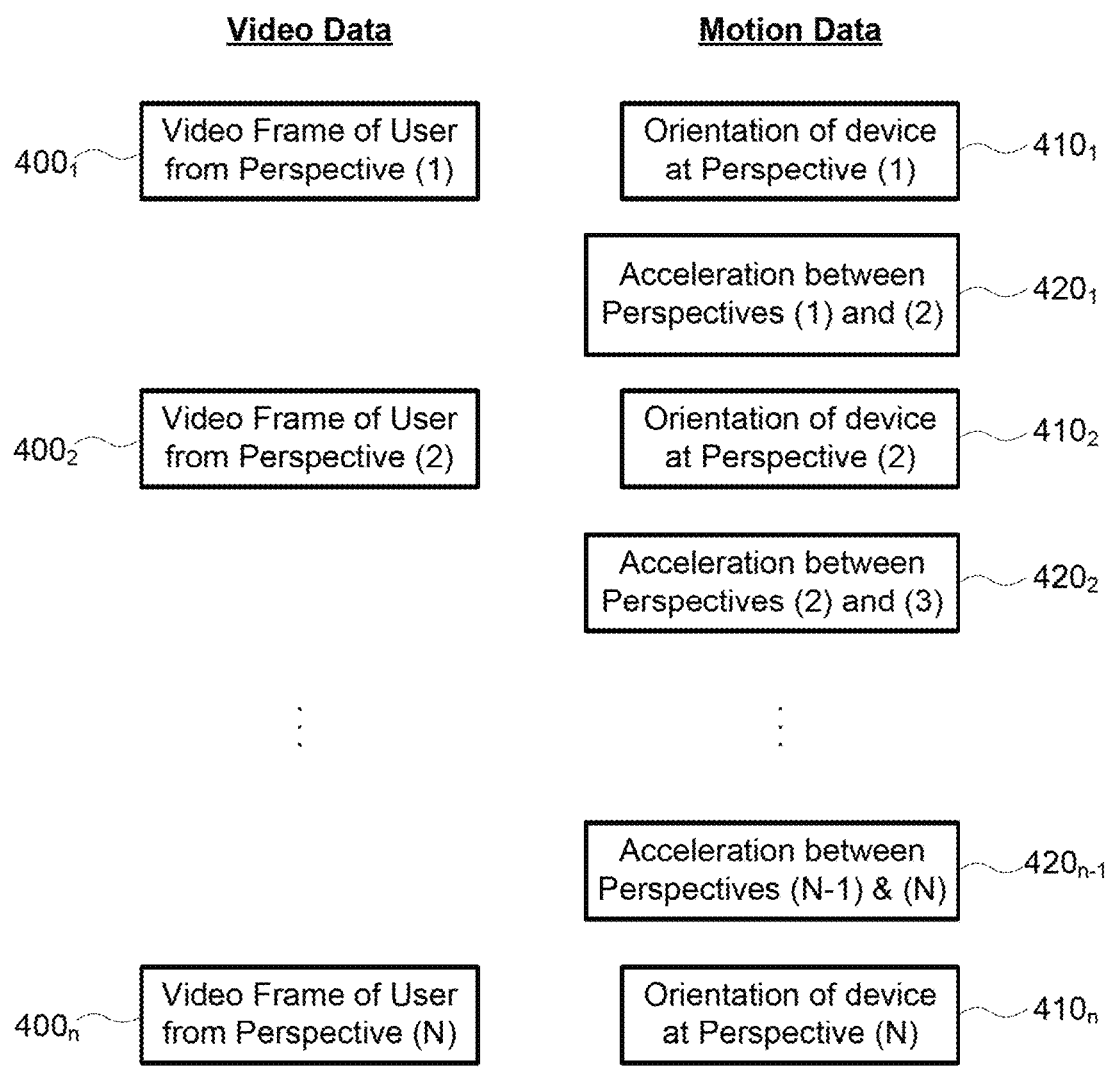
FIGS. 5A and 5B show the facial scan data collected and transmitted by the end user device in accordance with one form of the present technology.

The motion data may include an instantaneous orientation measurement at the time of and corresponding to one of the collected video frames, and may further include one or more acceleration measurements during or between each of the collected video frames, in order to track tilting and movement of the camera during the first video scan. FIG. 5A shows a diagram representing an example of the data that may be collected during a video scan. In the example of FIG. 4a, the data includes a plurality of video frames $400_1$-$400_n$ taken from a plurality of orientations 1-N (e.g., angles relative to the user's face). Each of the video frames may further be associated with time information (e.g., a timestamp) to indicate the specific time at which the frame was collected. The data further includes orientation information $410_1$-$410_n$ concerning an orientation of the camera for each given time that the video frames $400_1$-$400_n$ were collected. The data also includes motion information $420_1$-$420_{n-1}$ regarding a motion of the camera (e.g., three-dimensional acceleration measurements) between the specified times that each of the video frames $400_1$-$400_n$ were collected. Specifically, shown in FIG. 4a is motion information $420_1$ which concerns the motion of the camera between the time at which video frame $400_1$ and video frame $400_2$ were collected, motion information $420_2$ which concerns the motion of the camera between the time at which video frame $400_2$ and video frame $400_3$ (not shown) were collected, and motion information $420_{n-1}$ which concerns the motion of the camera between the time at which video frame $400_{n-1}$ (not shown) and video frame $400_n$ were collected. The orientation and motion information may be taken from an IMU file, or from other files containing data recorded by an IMU, accelerometer and/or gyrometer.

FIGS. 6A-6H show a user taking a video scan of their face from a plurality of angles relative to the user's face, in an example first video scan. In the example of FIGS. 6A-6H, the user first turns their head to the right (e.g., FIG. 6B), then to the right (e.g., FIG. 6E), and then tilts their head up (e.g., FIG. 6G).

Returning to FIG. 4, the device may also collect scale estimation data from which a relative scale or size of the user's face may be estimated. In some cases, the scale estimation data may be derived at least in part from information included in the first video scan data. In some cases, scale estimation data may be derived at least in part from other known information (e.g., technical specifications of the camera, manually input information about the user's face, etc.) Alternatively, and particularly in the example of FIG. 4, the scale estimation data may be derived from a second video scan of the user's face (at 308). Like the first video scan, the second video scan may include a plurality of video frames. However, unlike the first video scan, the frames in the second video scan may be taken from the same angle relative to the user's face, but from a plurality of distances. Again, the video frames (unlike photographs) may be sequenced such that identifiable landmark features of the user's face may be tracked frame-by-frame along the sequence of video frames.

The first and second video scans may be created as separate video files. Alternatively, the first and second video scans may be portions of a single video file. For example, the user (or another person) may take a single video of themselves, a first portion of such video involving the camera being held at various angles relative to the user's face, and a second portion involving the camera being moved towards and away from the user's face.

The device may optionally collect acceleration data (e.g., IMU data) data during the second video scan (at 310). The acceleration data may be correlated with the second video scan data, at this step or at a later step of processing (at 312), as with the optional correlation of the first video scan (e.g., using timestamp information associated with each of the video frames and with the collected motion data, using time delay information between the video data and acceleration data collection, etc.), such that an acceleration of the device may be measured as the videoed subject (e.g., the user's face) of the second video scan gets larger and smaller (as the device moves toward and away from the subject). The combination of the video scan data and acceleration data may be used to determine an estimated scale of the videoed subject.

Figure 5B:
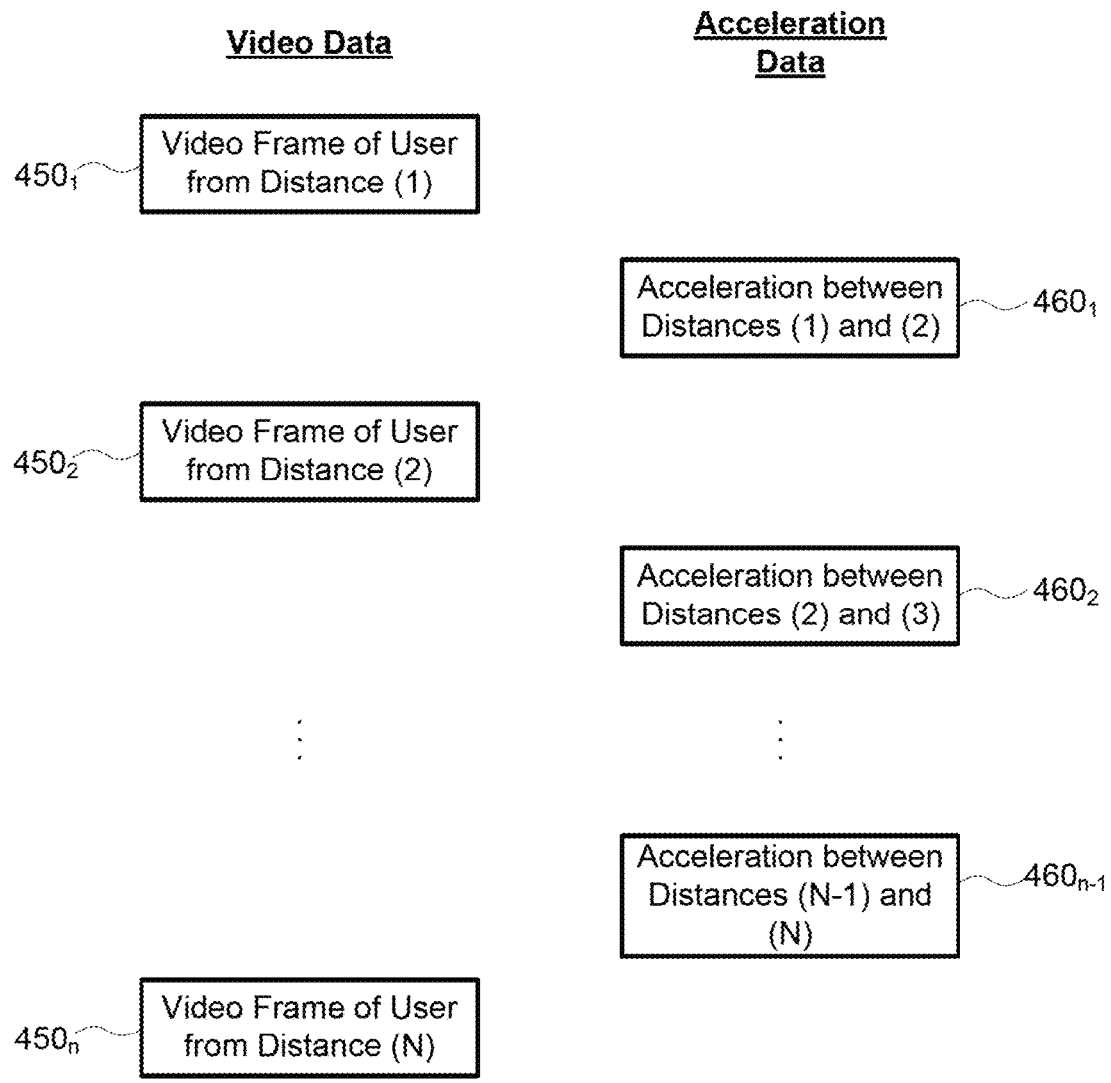
Figure 6A:
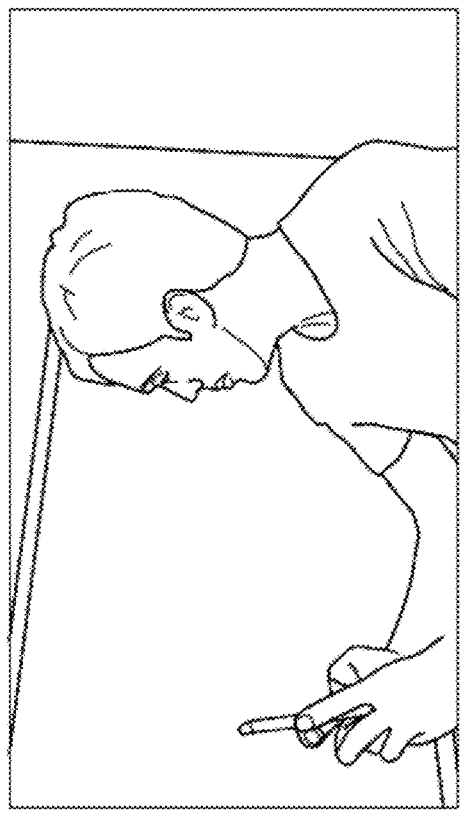
FIGS. 6A-6H show a user collecting facial scan data such as the data shown in FIG. 5A.
Figure 6B:
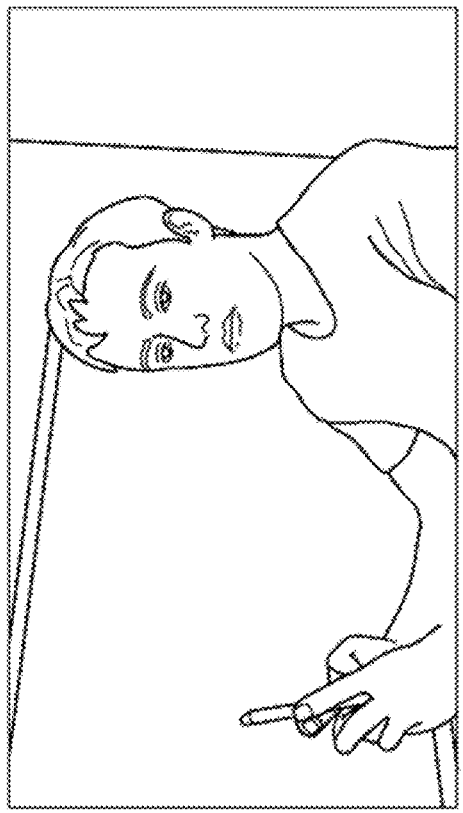
Figure 6C:
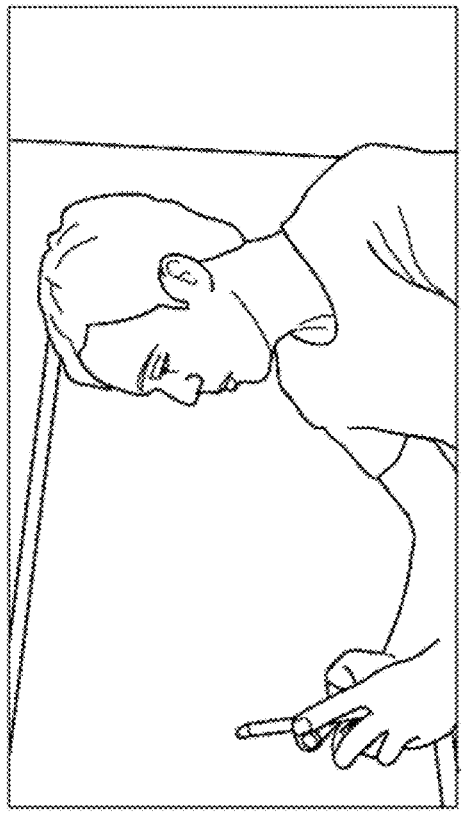
Figure 6D:
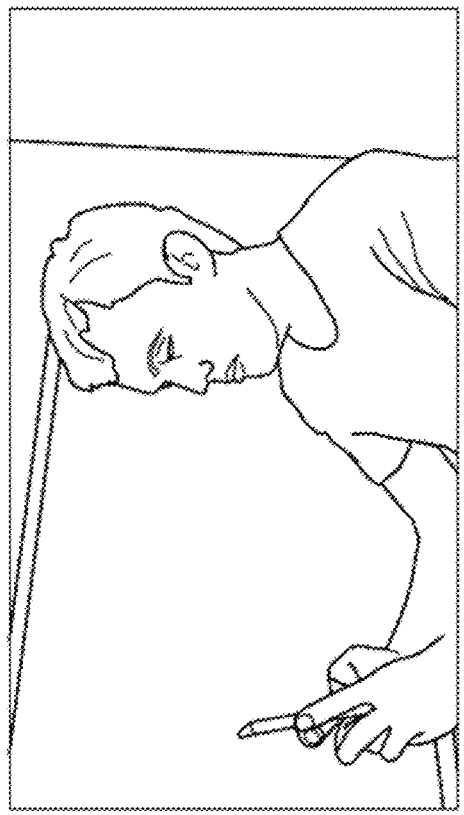
Figure 6E:
Figure 6F:
Figure 6G:
Figure 6H:
Figure 7A:
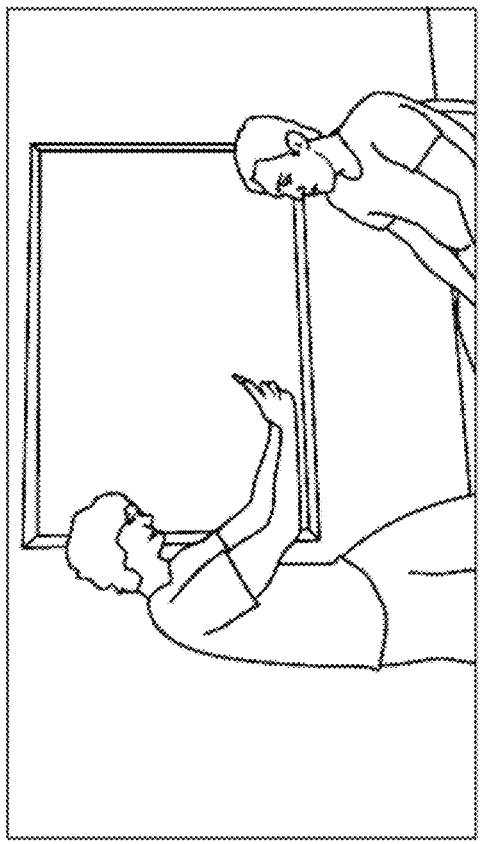
FIGS. 7A-7H show a user collecting facial scan data such as the data shown in FIG. 5B.
Figure 7B:
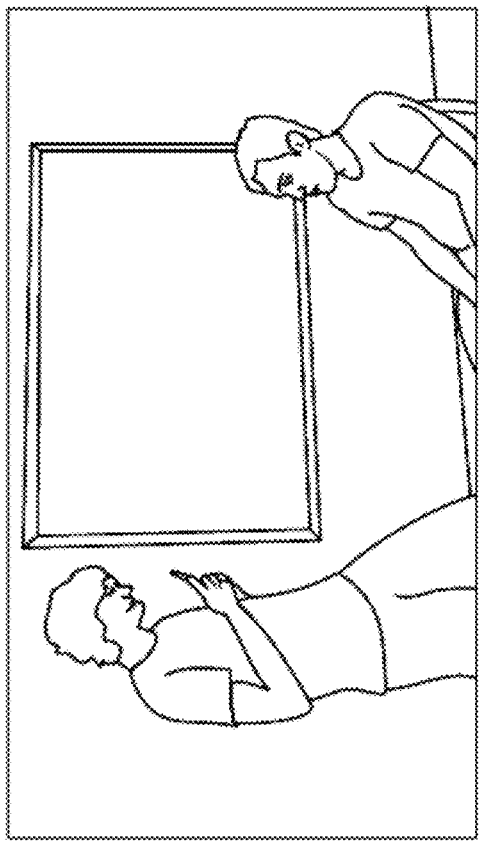
Figure 7C:
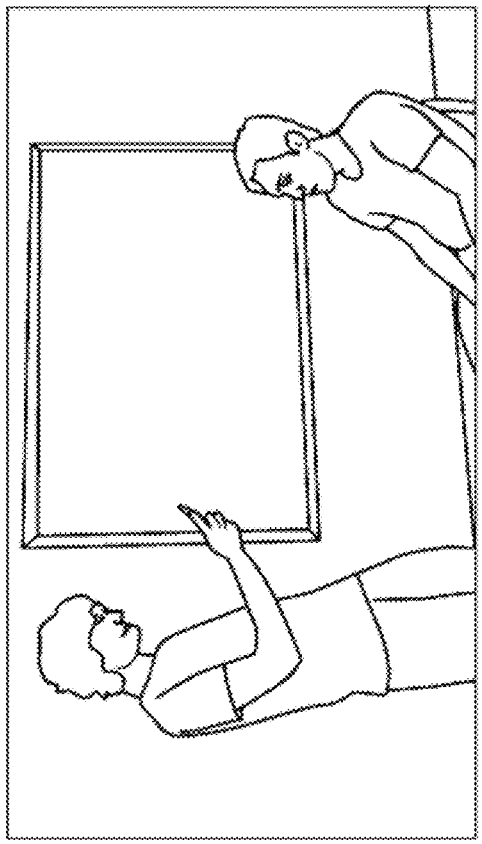
Figure 7D:
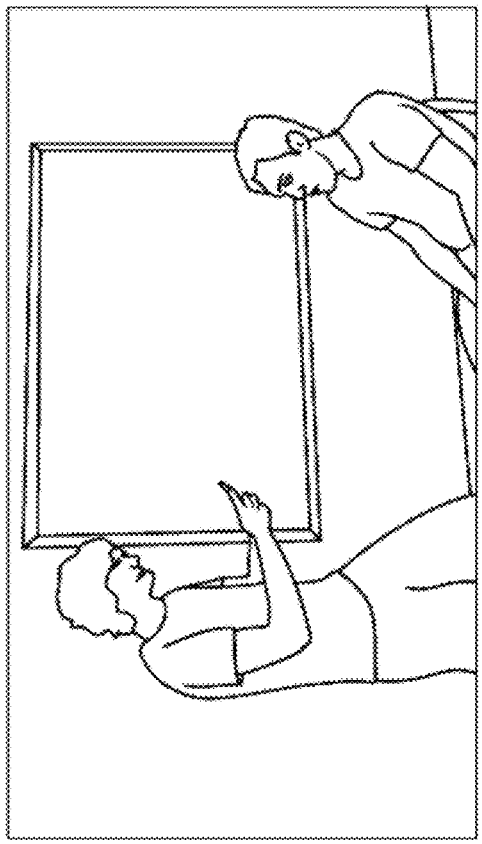
Figure 7F:
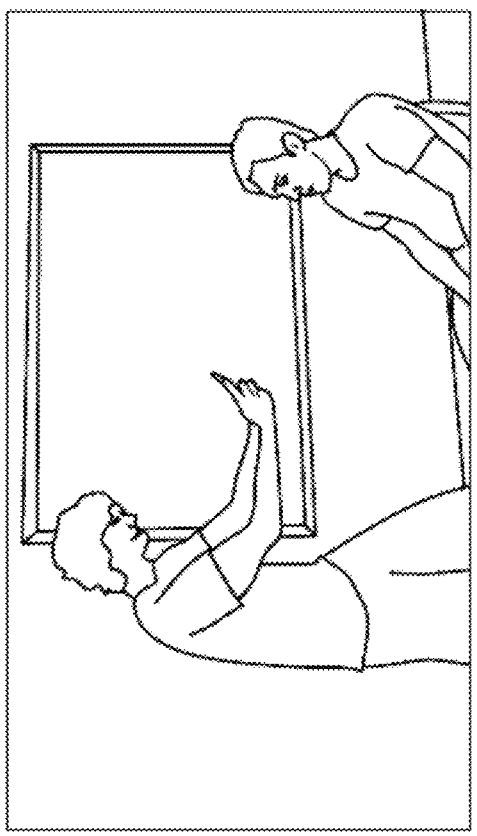
Figure 7H:
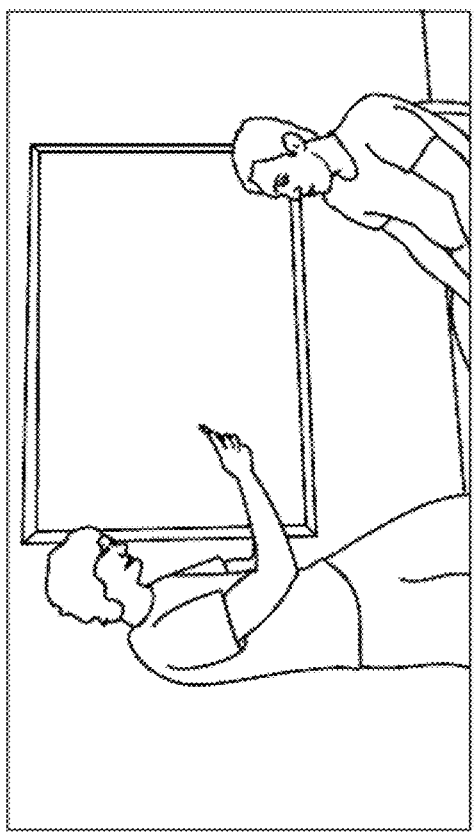
Figure 7E:
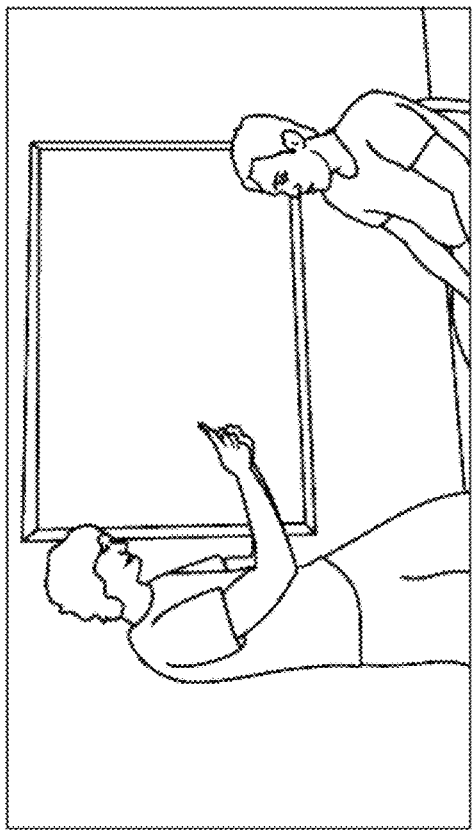
Figure 7G:
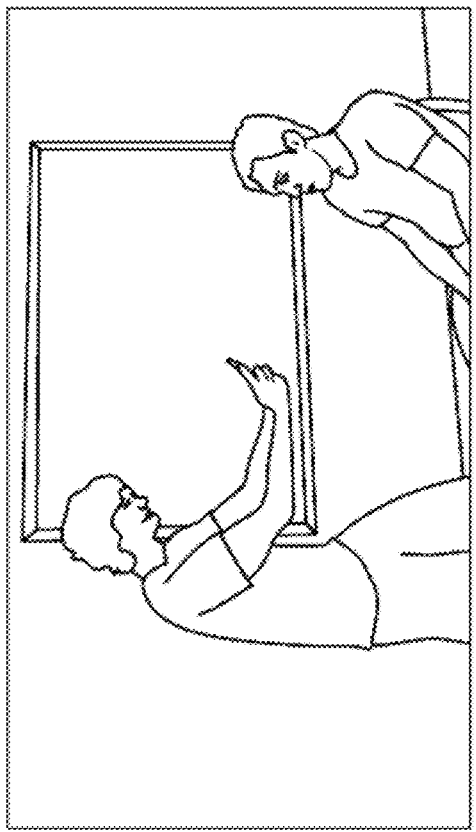

The acceleration data may include an acceleration measurement at about the time of a corresponding one of the collected video frames, or may include a plurality of acceleration measurements between each of the collected video frames, in order to track overall displacement of the camera during the second video scan. FIG. 5B shows a diagram representing an example of the data that may be collected during a second video scan. In the example of FIG. 5B, the data includes a plurality of video frames $450_1$-$450_n$ taken from a plurality of distances 1-N. Each of the video frames may further be associated with time information (e.g., a timestamp) to indicate the specification time at which the frame was collected. The data further includes information concerning an acceleration of the camera between the specified times of each of video frames $450_1$-$450_n$. Shown in FIG. 5B is acceleration data $460_1$, which concerns the acceleration of the camera between the time at which video frame $450_1$ and video frame $450_2$ were collected. Similarly, acceleration data $460_2$ concerns the acceleration of the camera between the time at which video frame $450_2$ and video frame $450_3$ (not shown) were collected. Acceleration data $460_{n-1}$ concerns the acceleration of the camera between the time at which video frame $450_{n-1}$ (not shown) and video frame $450_n$ were collected. The acceleration data may be taken from an IMU file, or other file containing data recorded by an accelerometer.

FIGS. 7A-7H shows a person taking a video scan of a user from a plurality of distances from the user's face, in an example second video scan. In the example of FIGS. 7A-7H, the camera is first moved in towards the user (e.g., FIG. 7B), then moved out away from the user (e.g., FIG. 7D), and then moved back in towards the user (e.g., FIG. 7F). Notably in those examples where acceleration data is collected with the video scan, the camera cannot be zoomed in and out but rather physically moved towards and away from the user.

In the case of the second video scan, acceleration data and video data may be correlated with one another based further on properties or features of the collected data itself, instead of solely based on timestamps. For example, identified features of the user's face may be measured in the individual frames of the video data. If there is determined to be a video frame for which a measured feature is largest, that video frame may be considered to have been taken at a greatest distance from the user's face. Thus, such a video frame may be correlated with a portion of the acceleration data determined to be collected at a distance farthest from the user's face (e.g., a point at which movement of the camera changes directions).

Returning again to FIG. 4, in some examples, a subset of video frames may be selected from the plurality of video frames collected during the video scan (at 314). This may be performed for either the first video scan or for the second video scan. In the case of both video scans, selecting the subset of video frames may be performed for purposes of efficiency. For instance, not all of the video frames of a video scan may be needed in order to track a user's facial features or to determine a scale of the user's face. In such a case, the device may only need to transmit a fraction or subset of the video frames, thus reducing bandwidth requirements (or speeding up) transmission of the video data.

The video frames selected to be transmitted may be chosen based on one or more criteria. For example, with regard to first video scan data, the video frames associated with profiles of the user's face that are considered important for determining the shape of the user's face (e.g., front profile, left profile, right profile, etc.) may be selected. For further example, with regard to the video scan data that is correlated with motion data (including acceleration data), it may be that the motion data is collected at a rate slower than the video data is collected, such that only some video frames have the same timestamp as the motion data. In such a case, the video data having a timestamp the same as some of the motion data may be selected.

As a further example, the system may specify a predetermined video frame rate (e.g., 60 frames per second, 240 frames per second) preferred for rendering three-dimensional surfaces based on video data, and may select a sufficient number of video frames to meet this frame rate without further exceeding the frame rate. In such a case, if the video data and motion data are to be correlated to one another, and if the motion data is captured at a rate greater than the predetermined video frame rate, the amount of motion data selected to be transmitted may similarly be reduced.

The device may then transmit the collected data (at 316). The collected data may include the video frames of the first video scan data, the video frames of the second video scan data (e.g., video files), and optionally motion data associated with the first video scan and acceleration data associated with the second video scan (e.g., IMU files, other data files). The device's transmitter/receiver may perform this transmission, thereby sending the collected data to a remote destination.

As explained above, in some cases, the transmitted data may be only a subset of the collected data if such subset of data is sufficient for constructing a three-dimensional surface of the user's face based on said data.

2.3 RENDERING A 3D SURFACE BASED ON FACIAL SCAN DATA

Once the data has been collected and transmitted by the end-user device (e.g., the end-user device 101 of FIG. 2), a processor (e.g., three-dimensional rendering engine (3D engine)) located remotely from the end-user device may receive and process the data in order to generate a three-dimensional surface representative of the user's face.

Figure 8:
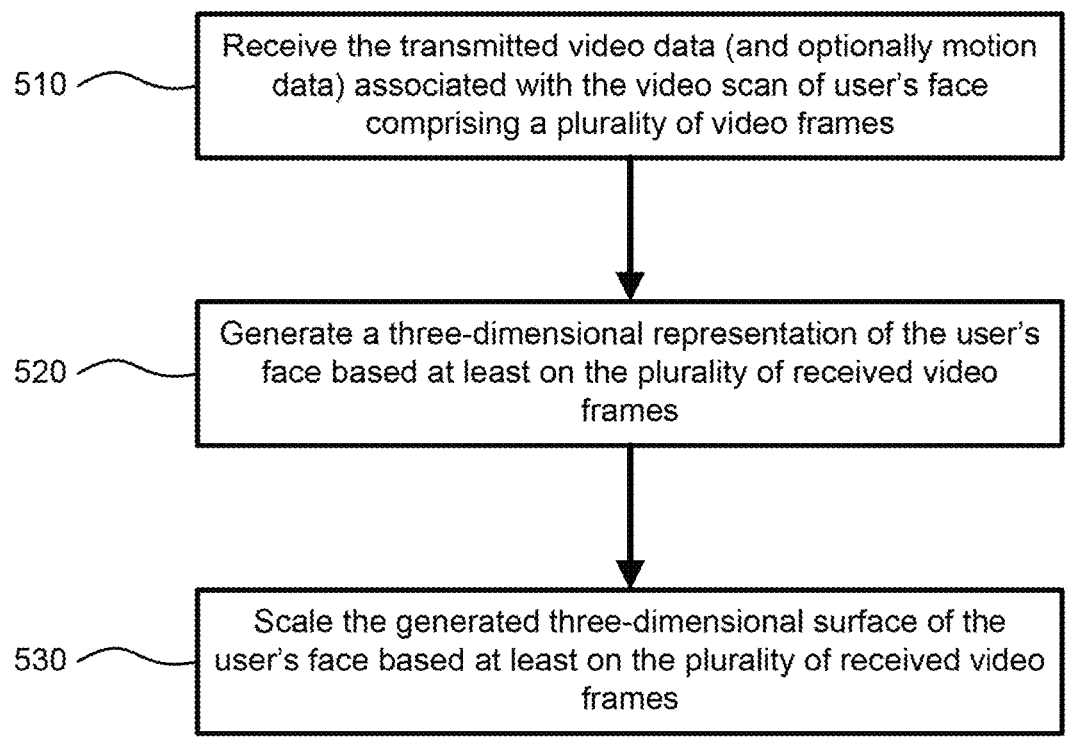
FIG. 8 shows a method of generating a three-dimensional surface representative of a user's face based on facial scan data, in accordance with one form of the present technology.

FIG. 8 is a flow diagram of an example method 500 for a processor to generate a three-dimensional surface. At 510, the processor receives the transmitted video data. This video data may be the video data associated with the first and second scans of the user's face described in connection with FIG. 4. The video data for the first video scan would include a plurality of video frames, the video frames having been taken from a plurality of angles relative to the user's face. As explained above, the plurality of video frames may be the complete first video scan, or a select portion or subset of the video frames from the first video scan. The video data for the second video scan would include a plurality of video frames, the video frames having been taken from a plurality of distances from the user's face.

In some cases, the processor may also receive motion data associated with the first video scan, as well as receive acceleration data associated with the second video scan.

2.3.1 Face Detection and Modeling

At 520, the processor generates a three-dimensional representation of the user's face based at least on the plurality of video frames of the received video data. Using the video data collected and transmitted in FIG. 4 as an example, the video data used at 520 would be the first video scan data. As explained above, the video frames of the first video scan include profiles of the user's face from a plurality of angles, such as a front profile, right side profile and left side profile, as well as other profiles with the user's head turned to the side or tilted up/down. Measurements of various facial features of the user, or anthropometric measurements, may be more accurately determined in one frame than another. For instance, the nasolabial angle may be more accurately determined from a side profile than a front profile, mouth width may be more accurately determined from a front profile, and upper lip height may be more accurately determined from a front profile with the user's head tilted slightly upwards. Various angles of video frames may be relied on for measurements of different facial features.

2.3.1.1 Face Detection

For any given video frame, in order for the processor to identify features of the user's face, the processor must initially detect the user's face in the video data. This may be accomplished using any face detection methodology known in the art. For example, the processor may search for features in the video frames (e.g., Haar-like features). The features may be representative of such features as the user's eyes (e.g., dark spot located vertically between light spots), the bridge of the user's nose (e.g., bright spot located horizontally between dark spots), and/or the user's eyes nose and mouth collectively (e.g., dark T-shaped spot between brighter spots for user's cheeks).

Detection of features may involve use of cascade classifiers (e.g., using Haar feature-based cascade classifiers), such that only a few classifiers may be needed to rule out portions of the video frames that do not portray the user's face, or do not portray a specific profile (e.g., front profile, side profile) of the user's face. Such classifiers help to increase the overall speed of performing feature detection.

Landmark features of the user's face may be identified based on the detected features. Landmark features may be points on the user's face that are tracked from frame to frame (e.g., a corner of the user's eye), or may be larger features as a whole (e.g., the user's eye) In either, boundaries between light and dark spots on the video frames may be used to identify the landmark features. Using the user's eye as an example, the edge of the user's eye may appear darker than the skin around it; therefore, the edges of the user's eye may be detected based on boundaries between bright and dark portions of a given video frame.

If the processor does not locate a face in a given frame of the received video data, the processor may disregard that frame (e.g., delete the frame from the received data set) for the remainder of the processing steps.

2.3.1.2 Morphable Standard Face Model

In one example of this specification, generating a three-dimensional surface representative of the user's face may further involve using a standard morphable face model.

The morphable face model begins with a three-dimensional surface representative of an average persons' face. Generally, the three-dimensional surface serves as a template from which to build a customized surface. The template surface may be a generic face, non-specific as to gender, age, or build of user. However, in some applications, it may be preferable to use a template that is a relatively generic face but at least partially biased towards gender, age and/or build factors. For instance, older individuals may be more likely to order a custom-fit CPAP mask than would a younger individual. Therefore, the template surface used for customizing a CPAP mask may be a generic face biased towards the shape or features of an older and/or overweight individual's face.

The morphable face model may then morph or adjust the template surface into a customized surface based on an analysis of the received plurality of video frames. The morphable face model may be configured to morph specific features of the user's face (e.g., nasolabial angle, alar angle, lip height, mouth width, nose width) based on information derived from the plurality of video frames. Such derived information may be obtained from an analysis of the landmark features identified in the video frame. For instance, if the width of the user's mouth in one video frame is determined to be larger than the mouth width of the template surface, then the mouth of the template surface may be morphed slightly to increase in width. In such a case, the degree of such morphing may be determined by several factors, such as the particular frame being evaluated (e.g., more weight for a front profile than a side profile when evaluating mouth width), or the number of frames in which the determination is made.

Changes to the template surface may be made as the plurality of video frames are being analyzed. For instance, a small morphing of the morphable surface may be made after each analyzed video frame. In such a case, the next video frame may be compared to the morphed template surface, or may still be compared to the initial template surface, in order to effect additional changes to the surface. For instance, a difference between an identified landmark feature of the analyzed video frame and a corresponding feature of the template surface may be calculated, and the calculated difference may be used to modify the template surface.

Alternatively, the changes to the template surface may be made after all of the plurality of video frames have been analyzed. In such a case, points and/or landmarks of the user's face may be identified and tracked frame-by-frame (as described below), and the morphable model may be generated based on those points and/or landmarks. Furthermore, the user's face may first be scaled (also as described below) prior to the morphable model being generated. In such cases, the morphable model may still improve the three-dimensional representation rendered from the tracked video frames by modifying the representation based on known characteristics of the user (e.g., age, gender, build, etc.).

2.3.1.3 Point-by-Point Feature Tracking

In another example, instead of using a template surface as a starting point for generating the custom three-dimensional surface, the custom surface may be generated entirely from points or features tracked in the plurality of video frames. The points may be the landmark features described above in connection with FIG. 8. Because the surface of a user's face includes many complex geometric features and contours, it may be desirable to track at least about 50 points on the user's face in order to generate a relatively accurate representation of the user's face. Additional points may be added, at the cost of computing power and/or computing time, in order to further improve accuracy of the three-dimensional surface. In some cases, about 80 points, about 132 points, or even more points may be used.

The points may be representative of (i) points of a user's face that are easily detectable using the processor, (ii) points of a user's face that are significantly variable from one individual to another, (iii) points of a user's face that are located in places where fitting apparatus or apparel on the user's face may ensure a seal against the user's face and/or may be prone to cause discomfort to the user (e.g., for a mask: around the user's mouth, for eyeglasses: on the bridge of the user's nose, etc.), (iv) points of a user's face that are related to measurements of the user's face (e.g., anthropometric measurements) to be derived from the analysis, or any combination of the above. In some examples, at least some of the points may be representative of the user's eyes, at least some of the points may be representative of the user's nose, and at least some of the points may be representative of the user's mouth. In other examples, at least some points may be representative of an edge of the user's face. The edge of the user's face may be defined as, for a given video frame, a boundary between the user's face and the background of the given video frame. Other features may also contribute to the defining the edge of the user's face, such as the user's ears and chin.

Aside from treatment of an edge of the user's face as a set of fixed points on the user's face, it may also be beneficial to identify, for each frame, a boundary between the user's face and the background of that frame. Because the boundary between the user's face and background may vary from frame to frame, the boundary may not be indicative of a particular landmark or point on the user's face. Nonetheless, in the same manner that a side profile view of the user's face may provide information regarding the particular contours of the user's nose, the shape of the boundary in video frames taken from other angles may provide information regarding contours along other parts of the user's face.

The points may be arranged in an array, such that the processor attempts to scale and fit the array to match with the detected features of the user's face. Spacing between points on the array is not fixed. This enables certain points to move independent of one another as the user turns or tilts their head in the video scan. Depth of certain facial features may be measured as the user turns or tilts their head. For example, considering the tip of the user's nose, if a first point is located to represent the tip of the user's nose, and a second point is located at the nasolabial groove, as the user turns to their left or right in the video scan, the first point will move a greater distance laterally than will the second point. The relative rates at which those points move may indicate a difference in distance from the camera, and thus indicate a depth dimension between those points. (Such depth may further be measured, or confirmed, based on a side profile video frame of the user.)

One drawback of searching for an array of points on the user's face is that, in some cases, when the user turns or tilts their head, some of the points of the array are no longer visible. The processor may then either incorrectly track those points on the video frame, or lose track of the user's face entirely. In order to avoid this drawback, it may be desirable that at least some of the points be grouped into discrete regions representative of larger features of the user's face (e.g., left eye, right eye, mouth, etc.).

In this regard, if some points of a given discrete region are not detectable, the processor may determine to cease detection of that discrete region, but may proceed to gather information about other discrete regions of the user's face. For example, if the user's left and right eyes are part of separate discrete regions, then if the user turns their head to the user's right, the user's right eye may drop out of the frames of the video scan and tracking of the right eye may be ceased, while tracking of the left eye, still in view, may continue to be performed. For further example, if the user's nose and eyes are part of separate discrete regions, then if the user tilts their head upwards, the user's eyes may drop out of the video scan and tracking of the eyes may be stopped, while tracking of the nose, still in view, may continue to be performed.

In those examples where points of the user's face are bundled into a discrete group (such as a number of points around the edge of a user's eye, or along a boundary of the user's lips) movement of those points may further be tracked as a group. In other words, the processor may recognize a coordinated motion of the identified group of points. In this regard, the movement of one point may influence the movement of other related points (e.g., movement of a point related to the left corner of a person's lips may indicate a similar movement of a point related to the right corner of the lips). Such "rules" may be used to further control the point-by-point tracking and increase overall accuracy of the tracked points.

In those examples where motion data (e.g., IMU data) correlated to the first video scan is provided, the motion data may provide further degree of stabilization to improve tracking points and/or measuring of features of the user's face.

Point-by-point tracking (or bundle tracking) may further be enhanced with the use of a machine learning algorithm. The machine learning algorithm may be trained to recognize the movement of individual points, or discrete groups of points, on a user's face based on a larger training dataset. The training dataset may be stored in a memory of the one or more servers, and may include a plurality of three-dimensional surfaces representative of a plurality of users' faces. The training dataset may further include information relating to identified points on those faces tracked along a series of frames.

As the machine learning algorithm evaluates more and more faces, it may learn how the individual points of a user's face tend to move as the face turns and tilts as a whole. The motion of the points on the faces of the larger dataset may further be manually evaluated, and the algorithm may be manually corrected in cases where points are not correctly tracked, thus further enhancing the algorithm's ability to learn from the training dataset.

The machine learning algorithm may be utilized to generate a support vector machine or other supervised learning model to classify and recognize points or landmarks on the user's face, frame by frame.

2.3.2 Face Scaling

Turning back to FIG. 8, at 530, the processor scales the three-dimensional representation of the user's face based at least on the plurality of video frames of the received video data.

Using the collected video data of FIG. 4 as an example, in some cases, the video data used for scaling may be from the first video scan. Specifically, the video data may be a front facing profile view of the user, in which a size of a preselected feature, or distance between two preselected features, may be measured to gain a relatively accurate measure of the scale of the user's face. In the case of using interpupil distance, for example, it has been found that the features of the user's face can be measured and scaled to within about 3 mm accuracy.

Alternatively, a marker (e.g., a sticker, QR code, etc.) with a known geometry (e.g., diameter) may be placed on the user's face, such that the distance of the camera from user's face for a given frame may be determined based on the size of the marker in the frame. Furthermore, the geometry of the marker (e.g., changes from circle to oval shape) may be tracked as the user turns and tilts their head, such that an angle of the camera relative to the user's face for a given frame may be determined based on the shape of the marker in the frame (or from changes in the shape of the marker from one frame to the next).

In a similar vein, the user may wear a mesh or mesh-like net over their face. The holes of the net may be of a known size, such that they function like a marker of known size on the user's face. Additionally, the holes of the net may be constructed with a known pattern or geometry, such that when the net is worn by the user, the shape of net deforms (e.g., conforms to contours of the user's face). The deformed shapes of the net may then be captured in the video frames, and analyzed to identify contours of the user's face.

Alternatively, instead of analyzing a geometric property of a marker in a captured video frame to determine scale, a distance of the user from the camera may be determined by placing a transmitter on the user's face and capturing a signal from the transmitter during the videoing process. For instance, the transmitter can emit a signal with a known signal strength, such that the strength of the received signal at the camera may be indicative of a distance between the camera and transmitter. In this case, the transmitter may further transmit time information, such that the signal strength measurements may be correlated to specific video frames based on the time information. (Alternatively, where transmit time is relatively negligible, the "time information" of the transmitted signal may be the time that such signal is received at the device), In this regard, distance (and thereby scale) may be calculated for every video frame, instead of only select video frames, based on the combination of received signal strength and time information at the camera.

As a further alternative, instead of measuring a feature shown in the video frame, a measurement of a given feature (e.g., nose width, interpupil distance, size of user's glasses) may be manually entered into the device by the user. In such cases, a single video frame may be chosen as the frame for measuring the manually input measurement. Optionally, the remaining video frames may be assumed to be taken from the same distance to the user as the chosen video frame.

In other cases, such as when tracking points of a user's face and scaling based on IMU data, it has been found that the points and features of the user's face may be measured and scaled within about 0.5 mm accuracy.

Alternatively, in some cases, the video data used for scaling may be from the second video scan, as well as from acceleration data collected in connection with the second video scan (e.g., IMU data). Knowing the acceleration of the camera from frame to frame (which itself involves correlating the acceleration data with the respective video frames), in combination with analyzing the relative size of the user as imaged from frame to frame, may provide sufficient information as to the user's actual distance from the camera during the second video scan. For example, the formula $\arg_s \min \eta\{s\nabla^2 p_v - Da_I\}$, as presented by Christopher Ham et al., *Hand Waving Away Scale*, Computer Vision—ECCV 2014: 13th European Conference, Zurich, Switzerland, Sep. 6-12, 2014 Proceedings, Part IV, may be used to determine the scale of a subject in a series of video frames in which the camera is accelerating (and decelerating) in a single dimension (e.g., towards and/or away from the subject). Once the actual scale of the video frame (stated differently, the actual distance of the user in a given video frame) is known, a scaling factor of the user's face may be determined.

The above methods of FIGS. 3 and 8 provide some examples of how a user can obtain a scaled three-dimensional rendering of their face using only their mobile phone or other camera-equipped portable communications device. However, there are other ways to obtain a scaled three-dimensional rendering of a user's face.

For example, the user may utilize two or more lenses to capture three-dimensional data of the user's face. In one such example, the mobile device may include two or more cameras (e.g., stereoscopic cameras) with a known distance between the cameras. Images from the two or more cameras may then be resolved with one another to derive a depth of the subject in the images (similar to how a pair of eyes provides depth perception).

In a similar vein, the user may utilize two or more devices for capturing video of the user's face. The two devices may communicate with each other wirelessly (e.g., Bluetooth). A linear distance between the devices may be determined based on signal strength of the communication signal therebetween. The linear distance may then be utilized in combination with the captured video frames from the two devices (which may be related to one another based on time information) in order to determine a scaling factor of the user's face.

Alternatively, instead of measuring signal strength between two devices, the two devices may be kept at a fixed distance from one another. For instance, the devices may be connected by a beam or shaft and caused to rotate around the users head.

In some cases, the devices may further be connected to a helmet that the user wears on their head. In such cases, instead of the devices being connected to one another, each of the devices may be mounted to a rotatable shaft mounted at the top of the helmet. The rotatable shaft may extend away from the user in the axial plane of the user. Each end of the rotatable shaft may be equidistant from the mounting point of the helmet, and may be connected to a corresponding arm extending downward from the shaft. The devices may be mounted from the respective arms such that each of the devices is held by the arm at about the height of the user's face and at a known distance away from the user. The arms may be rotated manually by the user, or automatically by a motor, thereby causing the devices to capture video of the user's face as they rotate around the user.

The rotatable shaft may also be fitted with a linear encoder to provide information about the angle of rotation. The linear encoder may further be synchronized with the video frames captured by the devices to provide input to later processing steps. Having the devices capture video frames of the user from a fixed distance means that the scaling factor of the user's face may be calibrated and known without having to analyze the video frames. Thus, in such cases, additional techniques or features to determine a scaling factor on a scan by scan basis are not necessary.

As an alternative to mounting two devices to a helmet, a single device may be used to capture video frames of the user from a plurality of angles without the device or user moving. This may be accomplished by positioning a rotatable prism between the device and the user, and further positioning a movable mirror behind the user (from the perspective of the device). The prism and mirror may be connected to one another using a rig, such that both the prism and mirror are mounted to the rig. The rig may be operable to rotate the mirror in a circle around the user such that the plane of the mirror is kept perpendicular to the user as it moves around the user. At the same time, the rig may be operable to rotate the prism in place. In one example, the mirror and prism may rotate in opposite directions (clockwise/counterclockwise, vice versa). Using the above described setup, images from all around the user may be captured by reflecting light through the prism and off the mirror. Since the distance between the device and user may be fixed and known (as well as the distance from the device to prism, prism to mirror, and mirror to user) scaling may be known without calculation or estimation.

Another way of measuring a scaling factor associated with a user's face involves use of a camera that includes an adjustable focus. Distance of the user's face from the camera may then be determined by adjusting the focal length until the face comes in and out of focus. In such a case, slices of the user's face at varying depths may be captured, and the three-dimensional model may be constructed from those slices.

Similarly, the camera may be capable of capturing video frames using different focal lengths simultaneously. The focal lengths may be adjusted to cause certain feature of the user's face to come in and out of focus. Given the focal lengths at which the features of the user's face come in and out of focus, and given further knowledge of the technical specifications of the camera, the distance of the user's face from the camera may be determined.

A further way of measuring a scaling factor associated with a user's face involves use of an ultrasonic and/or electromagnetic measuring device integrated with the camera. The device may be operable to emit an ultrasonic or electromagnetic signal, and measure the time delay between transmission and return of the reflected signal. The time delay may in turn be used to measure a distance between the camera and the user's face.

Alternatively, the device may be capable of emitting structured light, such as from a flash bulb. The pattern of the light may be cast on the user's face. Assuming that the pattern is known, the size of the pattern in a given video frame is indicative of the distance of the subject on which the light is cast.

In any of the above examples that utilize distance measurements taken during the capture of video frames of the user's face, such distance measurements may further be utilized in the generation of a 3D model of the user's face.

For instance, the distance information may be used to track a z-coordinate of the user's face (in and out of the video frame) if the distance between the device and face change at any time during the videoing process.

Furthermore, in any of the above examples, the three-dimensional surface engine may rely on the collected or known distance information in order to perform image stitching of the collected video frames.

2.4 USER ENROLMENT SYSTEM

In addition to capturing data sufficient for generating a three-dimensional rendering of a user's face, the end-user device may further be configured for communicating with a designer and/or vendor of custom-fit apparatus and apparel in order to order or purchase an article for the user based on the rendered surface.

In this regard, the same system used for taking a video scan of the user's face can also be used for enrolling the user in a service that designs articles based on the video scan. Such a user enrollment system may be constructed in the same manner as the system shown in FIG. 2, having one or more end-user devices connected to one or more servers. In the example of the user enrollment system, one or more servers may be dedicated for the purpose of gathering identification and/or enrollment information about a user, and one or more other servers may be dedicated for the purpose of collecting the user's video scans and rendering three-dimensional surfaces based on those scans. The user's rendered surface and personal information may likewise be stored in different databases or data stores. Such an arrangement may provide for additional security for the user's personal information on one secure database, without having to securely store excess amounts of data that do not require the same level of security (e.g., a de-indentified rendered surface of the user's face).

Figure 9:
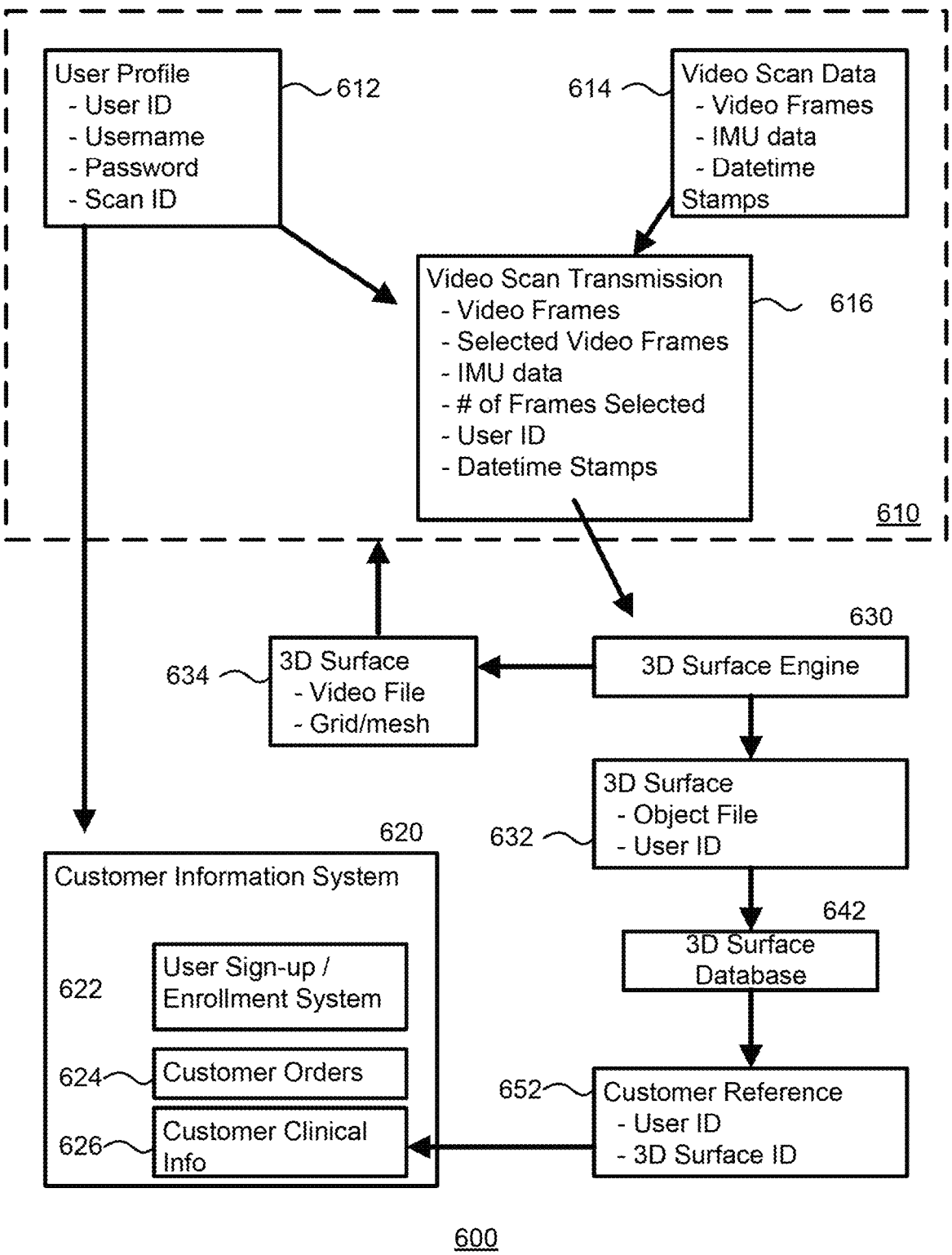
FIG. 9 shows an example system for user enrolment and ordering a custom-fit mask in accordance with one form of the present technology.

FIG. 9 shows a flow of information within an example user enrollment system 600. The user enrollment system 600 may include one or more end-user devices 610, a customer information system 620 (which is a subsystem of the user enrollment system 600), a three-dimensional surface engine (3D engine) 630, and one or more databases. In the example of FIG. 9, information may be generated at the end-user device 610, and subsequently transmitted to the customer information system 620 and 3D engine 630, or vice versa. Such information generated at the end-user device 610 may include a user profile 612 and video scan data 614. The user profile 612 may include such information as one or more unique identifiers of the user (including a unique identifier for the user's scans), a username of the user, a password. The video scan data 614 may include such information as the plurality of video frames from the video scan, motion and/or acceleration data (e.g., IMU data) from a built-in motion sensor, and datetime stamps identifying a specific time that the video frames and/or motion/acceleration data are collected.

The user profile 612, which includes personal information of the user, may be transmitted to the customer information system 620, where the user's personal information may be stored. The customer information system 620 also includes a sign-up or enrollment subsystem 622 for signing up or enrolling a user in a program for designing an apparatus or article for the user to wear on their face, as well as a database for storing customer orders 624. The customer information system 620 effectively serves as a hub for customers and vendors, so that a vendor who is contracted to design a customized apparatus or article for the user can easily and conveniently access the three-dimensional rendering of the user's face previously generated and uploaded by the user.

The customer information system 620 may further include clinical information, such as in a clinical information database 626, regarding the user. Clinical information may include any information that is important for a vendor to be aware of when designing the apparatus or article for the user (provided that the vendor is privileged to such information), and may further include information required for accessing the rendered surface of the user's face.

At the end-user side, in addition to transmitting information to a customer information system (e.g., customer information system 620 of FIG. 9), the user may also transmit information to other systems that provide services to customers, such as a processor or engine for rendering three-dimensional surfaces. In addition to the information already discussed above that may be relevant for rendering a three-dimensional surface (e.g., video scan data), additional information may be processed based on the video scan data. For instance, certain video frames may be selected, and the number of selected video frames may be recorded. A video scan transmission 616 from the end-user device 610 to the 3D engine 630 may then include the video frames and/or the selected video frames (in some cases, all of the video frames may be transmitted with the selected ones identified), the number of selected video frames, the motion/acceleration data, the user's unique identifier, and the datetime stamps. This information may then be used by the 3D engine 630 to produce a representation of a three-dimensional surface 632.

In the example of FIG. 9, the representation of the three-dimensional surface 632 includes an object file including the rendered surface representative of the user's face, as well as the user's unique identifier in order to associate the surface 632 with its user. However, in other examples of the disclosure, the representation may a plain text file including a list of data points, landmarks, measurements and/or other dimensions derived from analysis of the user's face in the video data. In such a case, the information of the text file may be utilized in order to customize an article associated with the user's face.

The three-dimensional surface 632 may be stored in a database 642 dedicated for storing object files. The object files may be stored de-identified, or anonymously. In other words, the object file may have a title or unique identifier other than the user's name or the user's unique identifier. The object file may then be accessed based on other information, such as a unique scan identifier, or a unique three-dimensional surface identifier. In the example of FIG. 9, the object file is assigned a unique three-dimensional surface identifier, which is associated with the user's unique identifier in a customer reference file 652 and stored in a separate location. Specifically, the customer reference file 652 is stored in a clinical information database 626 of the customer information system 620. Thus, the object file may be accessed based on the unique identifier of the user based on the customer reference file 652 stored at the customer information system.

In addition to rendering the three-dimensional surface object file, the 3D engine 630 may further compile a video file 634 simulating movement of the rendered surface. In the video file 634, the rendered surface may be shown as turning to the sides and/or tilting up and down in order that a viewer of the video file 634 may gain an understanding of the three-dimensional properties of the user's face based on the video. The rendered surface of the video file 634 may further include a superimposition of a grid over the user's face. The superimposed grid may close fit the contours of the user's face, such that the grid is indicative of changes in depth (e.g., indicating the edges of the user's face, indicating the sides and curvature of the user's nose, indicating roundness or flatness of the user's cheeks, etc.). Use of such a grid (or, similarly, a digitally rendered mesh) may further improve the viewer's understanding of the three-dimensional properties of the user's face. In some cases, the video file 634 may be transmitted from the 3D engine 630 back over the network to the end-user device 610.

In some examples, the customer information system 620, 3D engine 630 and databases 642/652 may be located across a plurality of servers in a network. The end-user device 610 may then connect to any of those remote servers over the network, either by wired or wireless connection.

Figure 10:
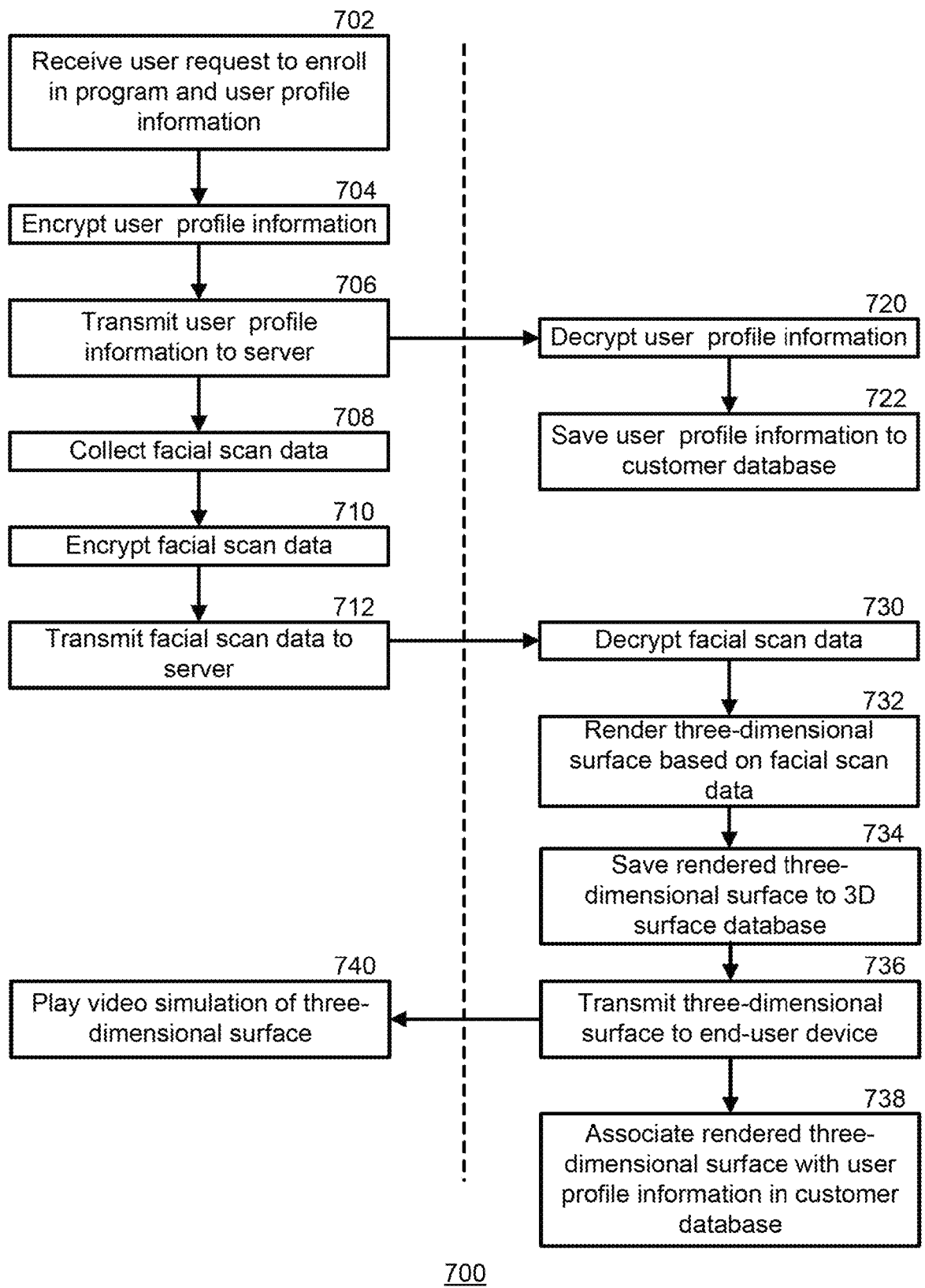
FIG. 10 shows a method of user enrolment and ordering a custom-fit mask, for example using the system of FIG. 9, in accordance with one form of the present technology.
Figure 11A:
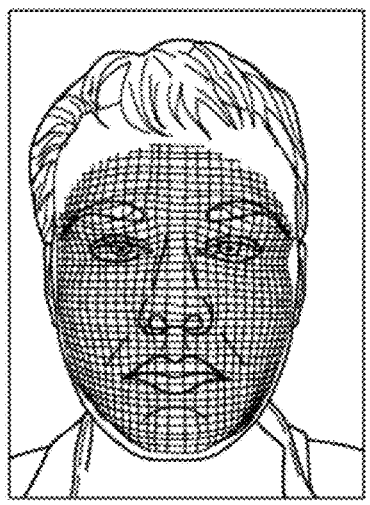
FIGS. 11A-11J show frames of a video file including a video scan of a user's face and superimposition of a grid over the three-dimensional representation.
Figure 11B:
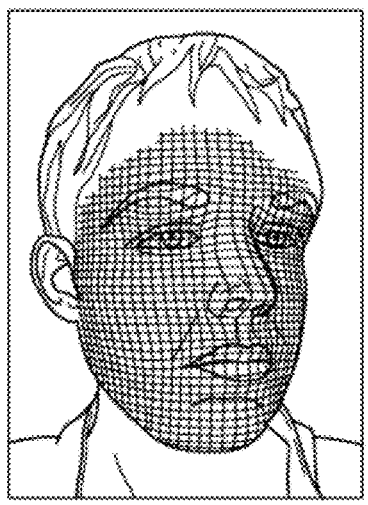
Figure 11C:
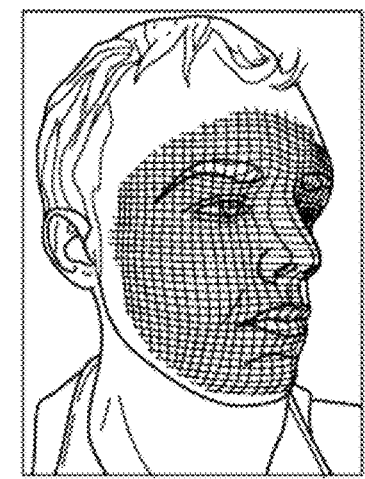
Figure 11D:
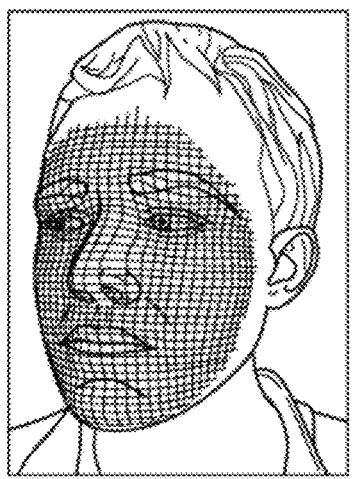
Figure 11E:
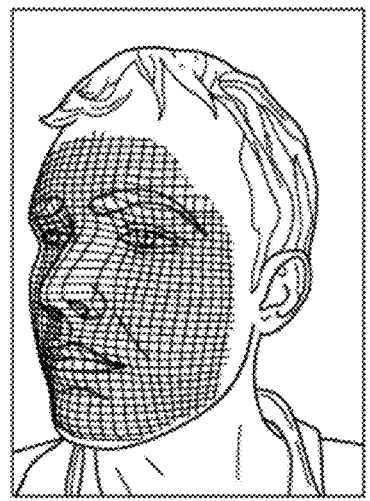
Figure 11F:
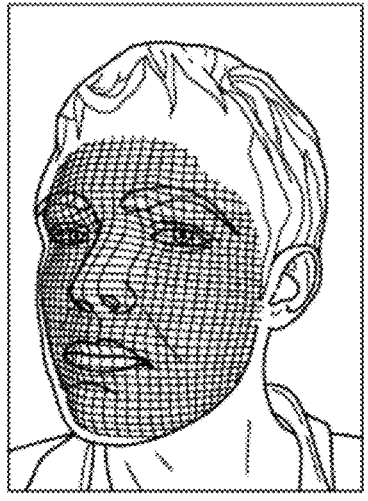
Figure 11G:
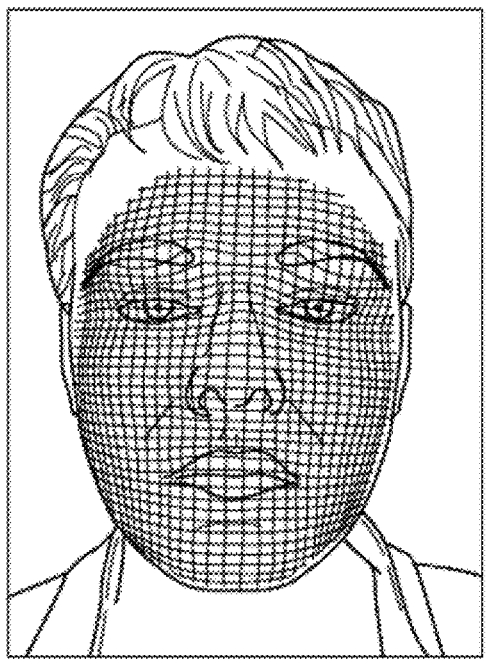
Figure 11H:
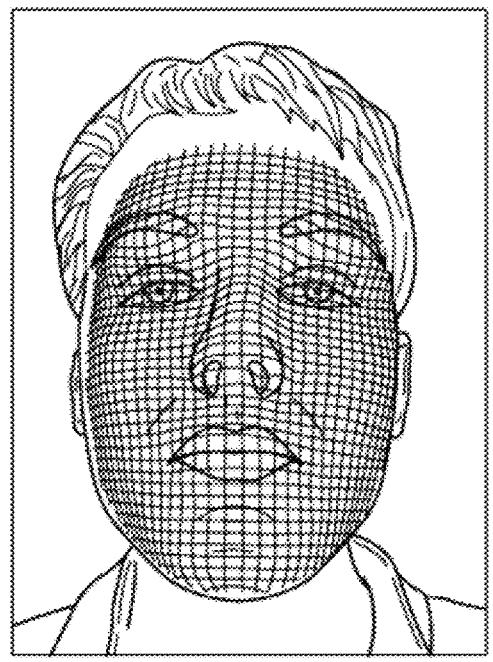
Figure 11I:
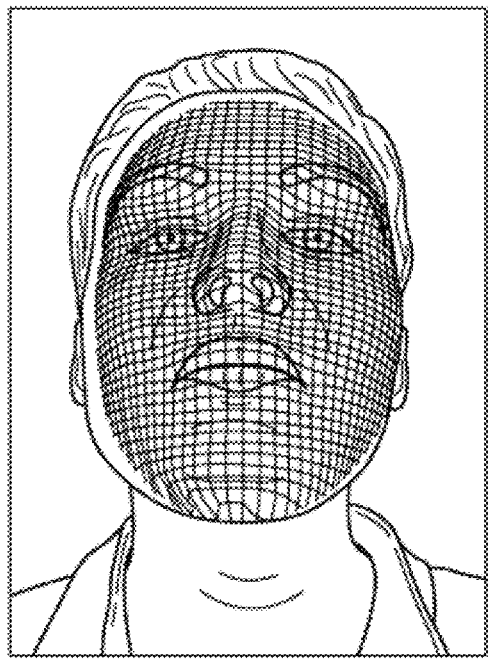
Figure 11J:
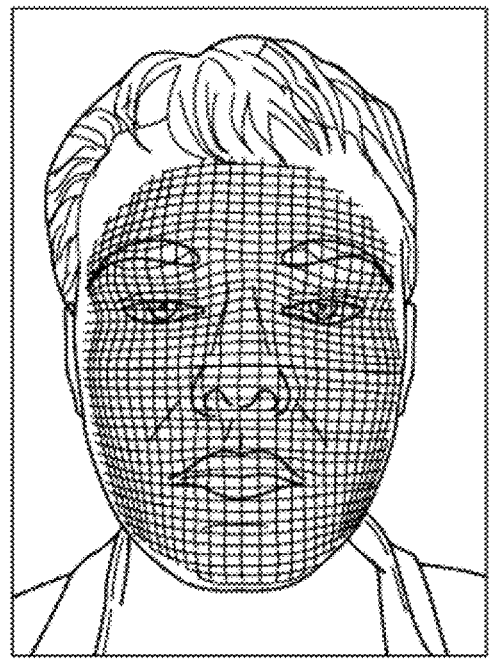

FIG. 10 shows an example flow diagram 700 of operations performed during use of a user enrollment system, such as the user enrollment system 600 of FIG. 9. At 702, an end-user device (e.g., in the example of FIG. 9, end-user device 610) receives an input from the user requesting to enroll in a program for designing a custom-fit mask. At 702, the device may also receive profile information of the user that may be used to create the user's profile in the enrollment program. At 704, the device may encrypt the user's profile information, and at 706 may transmit the user profile information to the customer information system (e.g., in the example of FIG. 9, customer information system 620).

At 720, the customer information system may receive and decrypt the user's enrollment request and profile information, including the unique identifier of the user. At 722, the profile information is stored in a customer database, where it may accessible to one or more vendors from whom the user purchases a custom-fit apparatus or other apparel.

At 708, the device may collect facial scan data based on a prompt from the user requesting that such facial scan data be collected. In the example of FIG. 10, the facial scan data may include any of the video frames and corresponding motion/acceleration data described previously in this specification. The facial scan data may also include timestamp information by which the video frames and other data may be temporally correlated to one another such that they may be combined during later processing (e.g., at the 3D engine).

The facial scan data may include each of profile images of the user as well as stabilization and/or scaling data (e.g., the first and second video scans of the example of FIG. 4). The facial scan data may also include information designating a pre-selected subset of video frames, such that a priority for using the preselected subset of video frames may be applied by the 3D engine during further processing. Along with the pre-selected subset of video frames may be an indication of the total number of pre-selected frames.

At 710, the facial scan data may be encrypted to secure transmission. At 712, the encrypted facial scan data may be transmitted, for instance to a remote processor, for three-dimensional rendering. The facial scan data may be encrypted and transmitted along with a request for production of a customized article (e.g., patient interface). The request may further include the unique identifier of the user so that the video scan data may be correlated to a specific user's face.

In the example of FIG. 10, the profile information and facial scan data is shown as being generally transmitted to the same remote location. However, the remote location may include multiple servers and or multiple processors, and the profile information and facial scan data may be transmitted to different servers and/or different processors for handling, processing and storage.

At 730, the processor decrypts the facial scan data, and at 732, the processor renders a three-dimensional surface based on the facial scan data. The three-dimensional surface may then be saved, at 734, to a database, such a dedicated database for such rendered surfaces. The three-dimensional surface may also, at 736, be transmitted back to the end-user device. The transmitted file may be a video file, which may be played back to the user by the end-user device at 740. FIG. 11 shows example frames from such a video file, in which a three-dimensional representation of a user's face turns side to side and tilts up and down, and further including a grid laid over the three-dimensional representation.

Lastly, at 738, the three-dimensional surface may be associated or otherwise linked with the user profile information in a customer database. The customer database may be separate from the three-dimensional surface database. A vendor who is interested in accessing the three-dimensional surfaces may interact with the associated information in the customer database instead of directly accessing the three-dimensional surface.

The above method illustrates how a user can, with a simple video scan from their mobile phone, conduct an online transaction that enables the design and production of a custom-fit article or apparatus. The customer information system may further include a marketplace to conduct and complete monetary transactions, so that user's may easily order, and vendors may easily fulfill orders for, customized wearables for the user's face. One application for this technology is for obtaining a mask or a patient interface for interfacing with a respiratory pressure therapy device such as a CPAP machine. For example, a processor may be configured to determine and/or identify a particular mask, mask-related component, mask size and/or size of a mask-related component, such as from a plurality of mask sizes and/or a plurality of sizes of mask-related components, based on the generated three dimensional surface. For example, a processor may be configured to compare dimensions from the generated three dimensional surface to associated dimensions of pre-existing interfaces, such as off-the-shelf respiratory masks (e.g., nasal, mouth and nose, etc. such as for a respiratory breathable gas therapy), to select a suitable size of such pre-existing interface or mask based on one or more dimensions of the rendered three dimensional surface and one or more dimensions of the pre-existing interfaces or masks. Thus, a selected mask with such an automated process may be offered, recommended to, or provided to the user based on dimensions from the rendered surface. In some cases to obtain a mask or mask component, one or more dimensions may be applied to a manufacturing process to custom manufacture such a mask or mask component for the particular user based on the one or more dimensions from the three dimensional rendered surface of the particular user. Thus, a processor, such as one of or associated with a manufacturing system, may be configured to determine one or more dimensions from the generated three dimensional surface for setting a manufacturing apparatus to produce a mask or mask component according to or based on the determined dimension(s). However, other articles such as glasses, sunglasses, costumes, etc., may also be customized using the same technology (e.g., video scans, enrollment system, etc.).

The following section provides some context regarding the design and manufacture of a patient interface that may be custom-designed in accordance with the above described technology.

2.5 PATIENT INTERFACE

Figure 12:
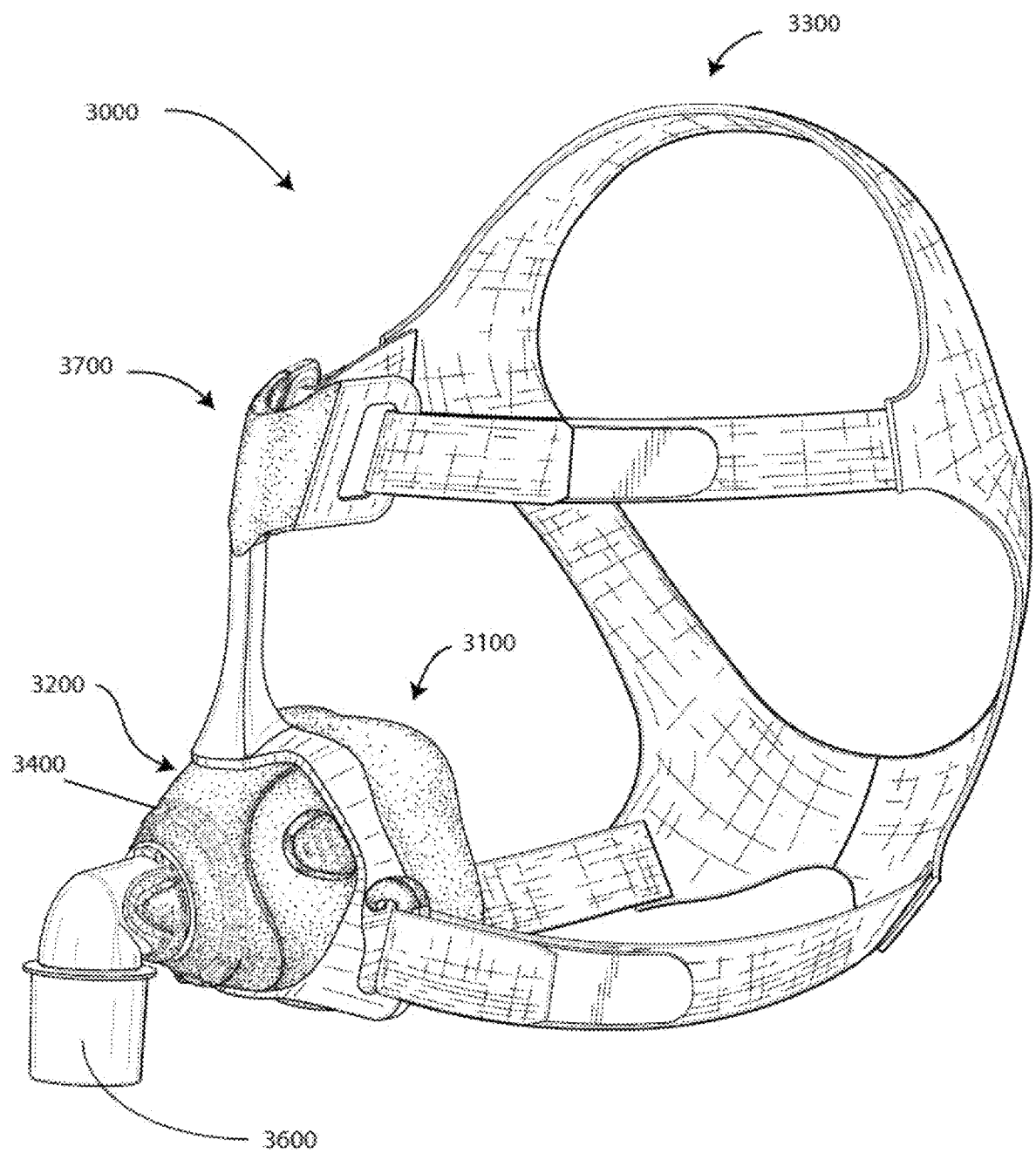
FIG. 12 shows a patient interface in the form of a nasal mask in accordance with one form of the present technology.

FIG. 12 shows a non-invasive patient interface 3000 in accordance with one aspect of the present technology. The patient interface comprises the following functional aspects: a seal-forming structure 3100, a plenum chamber 3200, a positioning and stabilizing structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

2.5.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. The sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

2.5.2 Plenum Chamber

The plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. The seal-forming structure 3100 may extend in use about the entire perimeter 3210 of the plenum chamber 3200.

2.5.3 Positioning and Stabilizing Structure

The seal-forming portion 3100 of the patient interface 3000 of the present technology may be held in sealing position in use by the positioning and stabilizing structure 3300.

In one form of the present technology, a positioning and stabilizing structure 3300 is provided that is configured in a manner consistent with being worn by a patient while sleeping. In one example the positioning and stabilizing structure 3300 has a low profile, or cross-sectional thickness, to reduce the perceived or actual bulk of the apparatus. In one example, the positioning and stabilizing structure 3300 comprises at least one strap having a rectangular cross-section. In one example the positioning and stabilizing structure 3300 comprises at least one flat strap.

In one form of the present technology, a positioning and stabilizing structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilizing structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilizing structure 3300 comprises a strap that is bendable and e.g. non-rigid. An advantage of this aspect is that the strap is more comfortable for a patient to lie upon while the patient is sleeping.

2.5.4 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel 3510.

2.5.5 Decoupling Structure(s)

In one form the patient interface 3000 includes at least one decoupling structure 3500, for example, a swivel 3510 or a ball and socket 3520.

2.5.6 Connection Port

Connection port 3600 allows for connection to the air circuit 4170.

2.5.7 Forehead Support

In one form, the patient interface 3000 includes a forehead support 3700.

2.5.8 Anti-Asphyxia Valve

In one form, the patient interface 3000 includes an anti-asphyxia valve 3800.

2.5.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

2.6 GLOSSARY

For the purposes of the present technology disclosure, in certain forms of the present technology, one or more of the following definitions may apply. In other forms of the present technology, alternative definitions may apply.

2.6.1 Anatomy of the Face

Ala: the external outer wall or "wing" of each nostril (plural: alar)

Alar angle: The angle formed between the pronasale and the ala.

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion

2.6.2 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame, in the context of a hardware component of a mask, will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurized above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

2.6.3 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

2.7 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

2.8 LABEL LIST system 100
end user device 101
memory 110
processor 120
algorithms 122
instructions 124
input interface 130
touch screen 131
keypad 132
microphone 133
accelerometer 134
gyrometer 136
camera 138
output interfaces 140
transmitter/receiver 145
server 151
memory 160
processor 170
algorithms 172
instructions 174
three dimensional rendering engine 176
wireless network 190
server 251
wireless network 290
example method 300
example method 500
user enrollment system 600
end user device 610
user profile 612
video scan data 614
video scan transmission 616
customer information system 620
enrollment subsystem 622
customer orders 624
clinical information database 626
engine 630
three dimensional surface 632
video file 634
database 642
customer reference file 652
example flow diagram 700
mobile end user devices $201_{a-d}$
patient interface 3000
seal-forming structure 3100
sealing flange 3110
support flange 3120
plenum chamber 3200
entire perimeter 3210
marginal edge 3220
structure 3300
vent 3400
decoupling structure 3500
swivel 3510
socket 3520
connection port 3600
forehead support 3700
anti-asphyxia valve 3800
video frame $400_1$
video frame $400_2$
video frame $400_3$
video frame $400_n$
video frame $400_{n-1}$
orientation information $410_1$
orientation information $410_n$
air circuit 4170
motion information $420_1$
motion information $420_2$
motion information $420_{n-1}$
video frame $450_1$
video frame $450_2$
video frame $450_3$
video frame $450_n$
video frame $450_{n-1}$
acceleration data $460_1$
acceleration data $460_2$
acceleration data $460_{n-1}$

The invention claimed is:

1. An apparatus for acquiring data for generation of a three-dimensional facial scan of a user for obtaining a patient respiratory interface component, the apparatus comprising:
an image sensor and lens for capturing two-dimensional video data of the user's face, the video data comprising a plurality of video frames;
a motion sensor configured to sense movement data of at least one of a movement of the apparatus and a change in orientation of the apparatus;
a processor configured to receive video data from the image sensor and to receive movement data from the motion sensor, to select a subset of the plurality of video frames in the video data based on one or more predetermined criteria, to generate a video file including the selected subset of the plurality of video frames, to generate a motion data file based on the movement data received from the motion sensor, and to associate each of the video file and motion data file with one another, wherein the video data and the movement data are collected at different rates and the subset of the plurality of video frames is selected based on a correlation of the subset of the plurality of video frames with the movement data; and
a transmitter, coupled with the processor, to transmit the associated video and motion data files to a system comprising a surface engine at a remote destination for generation of a three-dimensional representation of the user's face for obtaining a patient respiratory interface component based on the received selected subset of video frames and the received movement data.

2. The apparatus of claim 1, wherein the subset of the plurality of video frames is selected based on an association of each video frame in the subset to one or more predetermined views of the user's face.

3. The apparatus of claim 2, wherein the one or more predetermined views of the user's face comprises at least one front view of the user's face, one left profile of the user's face, and one right profile of the user's face.

4. The apparatus of claim 1, wherein the selected subset of the plurality of video frames comprises video frames having a time correspondence with the movement data.

5. The apparatus of claim 4, wherein video frames are correlated with the movement data based on time information of the video frames and of the movement data.

6. The apparatus of claim 5, wherein the time information includes time stamps.

7. The apparatus of claim 6 wherein the movement data is collected at a rate slower than the collection of the video data.

8. The apparatus of claim 1, wherein the subset of the plurality of video frames is selected to include a number of video frames that meet a predetermined video frame rate.

9. The apparatus of claim 8, wherein the processor is further configured to select a subset of the movement data received from the motion sensor.

10. The apparatus of claim 9 wherein an amount of movement data is reduced to correlate the amount of movement data with the predetermined video frame rate.

11. The apparatus of claim 1, wherein the motion sensor comprises at least one of an accelerometer and a gyrometer.

12. The apparatus of claim 1, wherein the motion sensor comprises an inertial measurement unit (IMU), and wherein the motion data file is an IMU file.

13. The apparatus of claim 1, wherein the apparatus is a mobile phone of the user.

14. A method for acquiring data for generation of a three-dimensional facial scan of a user for obtaining a patient respiratory interface component, the method comprising:
controlling an image sensor having a lens to capture two-dimensional video data of the user's face, the video data comprising a plurality of video frames;
sensing with a motion sensor configured to sense movement data of at least one of a movement of the image sensor and a change in orientation of the image sensor;
controlling, in a processor configured to receive video data from the image sensor and to receive movement data from the motion sensor, selection of a subset of the plurality of video frames in the video data based on one or more predetermined criteria, generation of a video file including the selected subset of the plurality of video frames, generation of a motion data file based on the movement data received from the motion sensor, and association of each of the video file and the motion data file with one another, wherein the video data and the movement data are collected at different rates and the subset of the plurality of video frames is selected based on a correlation of the subset of the plurality of video frames with the movement data; and
controlling, via a transmitter coupled with the processor, transmission of the associated video and motion data files to a system comprising a surface engine at a remote destination for generation of a three-dimensional representation of the user's face for obtaining a patient respiratory interface component based on the received selected subset of video frames and the received movement data.

15. The method of claim 14, wherein the subset of the plurality of video frames is selected based on an association of each video frame in the subset to one or more predetermined views of the user's face.

16. The method of claim 15, wherein the one or more predetermined views of the user's face comprises at least one front view of the user's face, one left profile of the user's face, and one right profile of the user's face.

17. The method of claim 14, wherein the selected subset of the plurality of video frames comprises video frames having a time correspondence with the movement data.

18. The method of claim 17, wherein video frames are correlated with the movement data based on time information of the video frames and of the movement data.

19. The method of claim 18, wherein the time information includes time stamps.

20. The method of claim 19 wherein the movement data is collected at a rate slower than the collection of the video data.

21. The method of claim 14, wherein the subset of the plurality of video frames is selected to include a number of video frames that meet a predetermined video frame rate.

22. The method of claim 21, wherein the processor is further configured to select a subset of the movement data received from the motion sensor.

23. The method of claim 22 wherein an amount of movement data is reduced to correlate the amount of movement data with the predetermined video frame rate.

24. The method of claim 14, wherein the motion sensor comprises at least one of an accelerometer and a gyrometer.

25. The method of claim 14, wherein the motion sensor comprises an inertial measurement unit (IMU), and wherein the motion data file is an IMU file.

26. The method of claim 14, wherein the method is performed on a mobile phone of the user.

27. A non-transitory processor-readable medium, having stored thereon processor-executable instruction which, when executed by one or more processors, cause the one or more processors to acquire data for generation of a three-dimensional facial scan of a user for obtaining a patient respiratory interface component, the processor-executable instructions configured to execute the method of claim 14.

28. An electronic system for enrolling an end-user for obtaining a patient respiratory interface component, the system comprising:
a customer information subsystem for receiving an enrolment request from an end-user device for obtaining a patient respiratory interface component, the enrolment request comprising a unique identifier of the end-user and for receiving from the end-user device a video file and a motion data file, the video file including video data comprising a subset of a plurality of video frames and the motion data file including movement data captured by the end-user device, the subset of the plurality of video frames selected based on one or more predetermined criteria, wherein the video data and the movement data are collected at different rates and the subset of the plurality of video frames is selected based on a correlation of the subset of the plurality of video frames with the movement data;
a three-dimensional surface rendering engine, including at least one processor, the three-dimensional surface rendering engine configured to render and scale a three-dimensional representation of the end-user's face for obtaining a patient respiratory interface component based on the selected subset of the plurality of video frames in the video file and the movement data in the motion data file; and
a first database for storing said rendered and scaled three-dimensional representation, or an identification of the rendered and scaled three-dimensional representation, in association with said unique identifier.

29. The system of claim 28, wherein the customer information subsystem and customer reference database operate on one or more servers in a network, and wherein the enrolment request and end-user video frame data and the movement data are received over the network.

30. The system of claim 29, wherein the three-dimensional surface rendering engine is configured to receive timestamp information, wherein the end-user video frame data and the movement data are combined at the three-dimensional surface rendering engine based on the timestamp information.

31. The system of claim 29, wherein one or more processors are configured to determine one or more dimensions from the rendered and scaled three-dimensional representation for obtaining the patient respiratory interface component.

32. The system of claim 31, wherein the one or more processors are configured to compare the one or more dimensions from the rendered and scaled three-dimensional representation with one or more dimensions from one or more respiratory masks.

* * * * *